(12) United States Patent
Cooke et al.

(10) Patent No.: US 6,821,992 B1
(45) Date of Patent: Nov. 23, 2004

(54) FUNGICIDES

(75) Inventors: Tracey Cooke, St. Albans (GB); David Hardy, Cambridge (GB); Brian Moloney, Oxon (GB); Peter Stanley Thomas, Cambridge (GB); Chris Richard Steele, Lyons (FR); Geoffrey Gower Briggs, Saint Didier au Mont d'Or (FR)

(73) Assignee: Aventis CropScience S.A. (FR)

( * ) Notice: Subject to any disclaimer, the term of this patent is extended or adjusted under 35 U.S.C. 154(b) by 101 days.

(21) Appl. No.: 10/049,976

(22) PCT Filed: Aug. 9, 2000

(86) PCT No.: PCT/EP00/08143
§ 371 (c)(1),
(2), (4) Date: Jul. 9, 2002

(87) PCT Pub. No.: WO01/11965
PCT Pub. Date: Feb. 22, 2001

(30) Foreign Application Priority Data

Aug. 18, 1999 (GB) .............................................. 9919499

Aug. 18, 1999 (GB) .............................................. 9919500

(51) Int. Cl.$^7$ ........................ A01N 43/40; C07D 213/00
(52) U.S. Cl. ........................ 514/336; 514/311; 514/332; 514/340; 514/342; 514/357; 546/176; 546/255; 546/271.1; 546/278.7; 546/329; 546/332; 546/336
(58) Field of Search ................................. 514/357, 336, 514/311, 332, 340, 342, 356; 544/333; 546/176, 255, 271.1, 278.7, 329, 332, 336

(56) References Cited

FOREIGN PATENT DOCUMENTS

| WO | 96/17840 | 6/1996 |
|----|----------|--------|
| WO | 99/42447 | 8/1999 |

Primary Examiner—Richard L. Raymond
(74) Attorney, Agent, or Firm—Osterlenk, Faber, Gerb & Soffen, LLP

(57) ABSTRACT

The invention relates to compounds of general formula I, where $A^1$, $R^1$, $R^2$ and Y are as defined in the description; and to their use as phytopathogenic fungicides.

5 Claims, No Drawings

FUNGICIDES

CROSS REFERENCE TO RELATED APPLICATIONS

This application is a national stage filing under 35 U.S.C. 371 of PCT application PCT/EP00/08143, filed Aug. 9, 2000, which claims priority from United Kingdom Application Nos. 9919499.5, filed Aug. 18, 1999, and 9919500.0, filed Aug. 18, 1999, the specifications of all of which are incorporated by reference herein. PCT Application PCT/EP00/08143 was published under PCT Article 21(2) in English.

This invention relates to compounds having fungicidal activity.

In a first aspect the invention provides the use of a compound of general formula I, complexes and salts thereof as phytopathogenic fungicides

(I)

where $A^1$ is a 2-pyridyl or its N-oxide, each of which may be substituted by up to four groups at least one of which is haloalkyl;

Y is a formula (D) or (E):

(E)

$A^2$ is heterocyclyl or carbocyclyl, each of which may be substituted;

$A^3$ is heterocyclyl or carbocyclyl, each of which may be substituted, or acyl;

L is a 3-atom linker, selected from the list: —N($R^5$)C(=X)N($R^6$)—, —N($R^5$)C(=X)CH($R^3$)—, —CH($R^3$)N($R^5$)CH($R^4$)—, —CH($R^3$)N($R^5$)C(=X)—, —N($R^3$)CH($R^4$)C(=X)— and —O—N($R^5$)C(=X)—; wherein $A^1$ is attached to the left hand side of linker L;

$L^1$ is a 4-atom linker selected from the list: —N($R^9$)C(=X)—$X^1$—CH($R^7$)—, —N($R^9$)C(=X)CH($R^7$)CH($R^8$)—, —N($R^9$)C(=X)C($R^7$)=C($R^8$)—, —N($R^9$)C($R^7$)=C($R^8$)—C(=X)—, —N($R^9$)C($R^7$)=C($R^8$)—SO$_2$—, —N($R^9$)C(=X)C($R^7$)($R^8$)—SO$_2$— and —N($R^9$)C(=X)C($R^7$)($R^8$)—$X^1$—; wherein $A^1$ is attached to the left hand side of linker $L^1$;

$R^1$, $R^2$, $R^3$, $R^4$, $R^7$ and $R^8$, which may be the same or different, are $R^b$, cyano, nitro, halogen, —OR$^b$, —SR$^b$ or optionally substituted amino;

$R^5$ and $R^6$ which may be the same or different, are $R^b$, cyano or nitro; or any $R^1$, $R^3$ or $R^5$ group, together with the interconnecting atoms, can form a 3-, 4-, 5- or 6-membered ring with any $R^2$, $R^4$ or $R^6$ or any $R^1$, $R^2$, $R^3$, $R^4$, $R^5$ or $R^6$ group, together with the interconnecting atoms can form a 5- or 6-membered ring with $A^2$; or $R^1$ or $R^2$, or $R^7$ or $R^8$, together with the interconnecting atoms, may form a 3-, 4-, 5- or 6-membered ring, which may be substituted;

$R^b$ is alkyl, alkenyl, alkynyl, carbocyclyl or heterocyclyl, each of which may be substituted, or hydrogen or acyl;

X is oxygen or sulfur;

$X^1$ is oxygen, sulfur or —N($R^9$)—, and $R^9$ is $R^b$, cyano or nitro, or $R^9$ and $A^3$, $R^1$, $R^2$, $R^7$ and $R^8$, together with the interconnecting atoms, may form a 3-, 4-, 5- or 6-membered ring, which may be substituted.

Preferred substituents on the 2-pyridyl group ($A^1$) are halogen, hydroxy, cyano, nitro, SF$_5$, trialkylsilyl, optionally substituted amino, acyl, or a group —$R^a$, —OR$^a$ or —SR$^a$, or a group —C($R^a$)=N—Q, where Q is —$R^a$, —OR$^a$, —SR$^a$ or optionally substituted amino, wherein $R^a$ is alkyl, alkenyl, alkynyl, carbocyclyl or heterocyclyl, each of which may be substituted; or two adjacent substituents together with the atoms to which they are attached form an optionally substituted ring which can contain up to 3 hetero atoms. Preferably, the 2-pyridyl group is substituted at the 3 and/or 5 position.

Preferred compounds are those in which one or more of the following features are present:

$A^2$ is optionally substituted phenyl, optionally substituted heterocyclyl, optionally substituted cyclohexyl or optionally substituted cyclopropyl; or $A^3$ is optionally substituted phenyl, optionally substituted heterocyclyl or acyl; or $R^1$, $R^2$, $R^3$, $R^4$, $R^7$ and $R^8$ are hydrogen, optionally substituted alkyl, optionally substituted phenyl, cyano, acyl or halogen (more preferably $R^1$ and $R^2$ are hydrogen); or $R^5$ and $R^6$ are hydrogen, optionally substituted alkyl or acyl; or $R^7$ and $R^8$ are hydrogen, optionally substituted alkyl or acyl; or $R^9$ is hydrogen or optionally substituted alkyl; or the 2-pyridyl group ($A^1$) is substituted by alkoxy, alkyl, cyano, halogen, nitro, alkoxycarbonyl, alkylsulfinyl, alkylsulfonyl or trifluoromethyl, (preferably chlorine or trifluoromethyl).

Many of the compounds of formula I are novel. Therefore, according to a further aspect, the invention provides compounds of formula I where:

Y is —L—$A^2$— and;

L is —NHC(=X)NH—; and $A^2$ is phenyl optionally substituted by halogen, haloalkyl, phenoxy, alkoxy, alkyl, CN, NO$_2$, SO$_2$—(N-tetrahydropyridinyl), alkylthio, acyl, phenylsulphonyl, dialkylamino, alkylsulphonyl, benzylsulphonyl, S(phenyl substituted by halogen); or $A^2$ is cycloalkyl; or naphthyl optionally substituted by NO$_2$; or L is —NHC(=O)CH($R^3$)—;

$R^3$ is hydrogen, alkyl, phenyl, halogen or acyloxy;

$A^2$ is phenyl optionally substituted by halogen, NO$_2$ or alkoxy; or thienyl; or imidazolyl; or pyrrolinyl substituted by alkoxy; or L is —CH($R^3$)N($R^5$)CH$_2$—;

$R^3$ is N-alkylcarbamoyl or akoxycarbonyl;

$R^5$ is hydrogen or acyl;

$A^2$ is phenyl optionally substituted by alkyl, alkoxy, halogen, NO$_2$, haloalkyl or phenoxy; or is naphthyl; or L is —CH($R^3$)NHC(=O)—;

$R^3$ is N-alkylcarbamoyl or alkoxycarbonyl;

$A^2$ is phenyl optionally substituted by alkoxy, halogen, NO$_2$, haloalkyl, phenoxy or phenyl; or is cycloalkyl; or L is —O—NHC(=O)— and $A^2$ is phenyl substituted by alkyl; or Y is —L¹—A³— and;

L¹ is —NHC(=O)(CH$_2$)$_2$—, and A³ is phenyl substituted by alkyl; or

L¹ is —NHC(=S)NHCH$_2$—, and A³ is phenyl; or

L¹ is —NHC(=O)CH(alkyl)S—, and A³ is phenyl; or

L¹ is —NHC(=O)OCH$_2$—, —NHC(=O)(CH$_2$)$_2$—, —NHC(=O)NHCH$_2$—, —NHC(=S)NHCH$_2$—, —N(alkyl)C(=O)CH$_2$O— or —NHC(=O)CH$_2$O—;

R¹ is hydrogen;

R² is hydrogen or alkoxycarbonyl;

A³ is phenyl optionally substituted by halogen, alkyl, phenyl, OH, alkoxy or alkoxycarbonyl; or fluorenyl; or pyridyl optionally substituted by halogen or haloalkyl; or thiadiazolyl substituted by alkyl; or benzthiazolyl optionally substituted by halogen or by phenyl substituted by halogen; or quinolinyl substituted by haloalkyl; or triazolyl substituted by alkyl or phenyl; or tetrazolyl substituted by alkyl or cycloalkyl; or pyrimidinyl substituted by alkyl; or benzoxazolyl; or imidazolyl substituted by alkyl; or thiazolinyl substituted by alkyl and methylene; or L¹ is —NHC(=O)CH(R⁸)N(R⁹)—;

R¹ is hydrogen;

R² is hydrogen or alkyl;

R⁸ and R⁹ are each hydrogen or alkyl;

A³ is benzoyl optionally substituted by alkyl; or benzyloxycarbonyl; or alkoxycarbonyl; or L¹ is —NHC(=O)CH(alkyl)SO$_2$—;

R¹ and R² are each hydrogen;

A³ is phenyl; or

L¹ is —NHC(=O)CH$_2$X¹—, where X¹ and A³ form a 2-oxo-N-benzthiazolyl ring which is substituted by halogen; and R¹ and R² are each hydrogen.

The invention also includes any of the compounds specifically exemplified hereinafter.

Any alkyl group may be straight or branched and is preferably of 1 to 10 carbon atoms, especially 1 to 7 and particularly 1 to 5 carbon atoms.

Any alkenyl or alkynyl group may be straight or branched and is preferably of 2 to 7 carbon atoms and may contain up to 3 double or triple bonds which may be conjugated, for example vinyl, allyl, butadienyl or propargyl.

Any carbocyclyl group may be saturated, unsaturated or aromatic, and contain 3 to 8 ring-atoms. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Any heterocyclyl group may be saturated, unsaturated or aromatic, and contain 5 to 7 ring-atoms up to 4 of which may be hetero-atoms such as nitrogen, oxygen and sulfur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Any alkyl, alkenyl, alkynyl, carbocyclyl or heterocyclyl group, when substituted, may be substituted by one or more substituents, which may be the same or different, and may be selected from the list: hydroxy; mercapto; azido; nitro; halogen; cyano; acyl; optionally substituted amino; optionally substituted carbocyclyl; optionally substituted heterocyclyl; cyanato; thiocyanato; —SF$_5$; —OR$^a$; —SR$^a$ and —Si(R$^a$)$_3$, where R$^a$ is alkyl, alkenyl, alkynyl, carbocyclyl and heterocyclyl, each of which may be substituted. In the case of any carbocyclyl or heterocyclyl group the list includes additionally: alkyl, alkenyl and alkynyl, each of which may be substituted. Preferred substituents on any alkyl, alkenyl or alkynyl group are alkoxy, haloalkoxy or alkylthio, each containing 1 to 5 carbon atoms; halogen; or optionally substituted phenyl. Preferred substituents on any carbocyclyl or heterocyclyl group are alkyl, haloalkyl, alkoxy, haloalkoxy or alkylthio, each containing 1 to 5 carbon atoms; halogen; or optionally substituted phenyl.

In the case of any alkyl group or any unsaturated ring-carbon in any carbocyclyl or heterocyclyl group the list includes a divalent group such as oxo or imino, which may be substituted by optionally substituted amino, R$^a$ or —OR$^a$. Preferred groups are oxo, imino, alkylimino, oximino, alkyloximino or hydrazono.

Any amino group, when substituted and where appropriate, may be substituted by one or two substituents which may be the same or different, selected from the list: optionally substituted alkyl, optionally substituted amino, —OR$^a$ and acyl groups. Alternatively two substituents together with the nitrogen to which they are attached may form a heterocyclyl group, preferably a 5 to 7-membered heterocyclyl group, which may be substituted and may contain other hetero atoms, for example morpholino, thiomorpholino or piperidinyl.

The term acyl includes the residues of sulfur and phosphorus-containing acids as well as carboxylic acids. Typically the residues are covered by the general formulae —C(=X$^a$)R$^c$, —S(O)$_p$R$^c$ and —P(=X$^a$)(OR$^a$)(OR$^a$), where appropriate X$^a$ is O or S, R$^c$ is as defined for R$^a$, —OR$^a$, —SR$^a$ optionally substituted amino or acyl; and p is 1 or 2. Preferred groups are —C(=O)R$^d$, —C(=S)R$^d$, and —S(O)$_p$R$^d$ where R$^d$ is alkyl, C$_1$ to C$_5$ alkoxy, C$_1$ to C$_5$ alkylthio, phenyl, heterocyclyl or amino, each of which may be substituted.

By the term "salts" is meant salts the cations or anions of which are known and accepted in the art for the formation of salts for agricultural or horticultural use. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, e.g. formed by compounds of formula I containing an amino group, include salts with inorganic acids, for example hydrochlorides, sulphates, phosphates and nitrates and salts with organic acids for example acetic acid.

Complexes of compounds of the invention are usually formed from a salt of formula MAn$_2$, in which M is a divalent metal cation, e.g. copper, manganese, cobalt, nickel, iron or zinc and An is an anion, e.g. chloride, nitrate or sulfate.

In cases where the compounds of the invention exist as the E and Z isomers, the invention includes individual isomers as well as mixtures thereof.

In cases where compounds of the invention exist as tautomeric isomers, the invention includes individual tautomers as well as mixtures thereof.

In cases where the compounds of the invention exist as optical isomers (for example where $R^1$ and $R^2$ are different), the invention includes individual isomers as well as mixtures thereof.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), late tomato or potato blight (*Phytophthora infestans*), apple scab (*Venturia inaequalis*), and glume blotch (*Leptosphaeria nodorum*). Other fungi against which the compounds may be active include other powdery mildews, other rusts, and other general pathogens of Deuteromycete, Ascomycete, Phycomycete and Basidomycete origin.

The invention thus also provides a method of combating fungal pests such as phytopathogenic fungi at a locus infested or liable to be infested therewith, which comprises applying to the locus a compound of formula I or a complex or salt thereof.

The invention also provides an agricultural composition comprising a compound of formula I or a complex or salt thereof in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal, acaricidal, antimicrobial or antibacterial properties. Alternatively the compound of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or alkyl phenol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine; the dialkyl sulfosuccinates, e.g. the sodium sulfonate of dioctyl succinate; acid derivatives of alkyl glycosides and alkylpolyglycosides materials and their metal salts, e.g. alkyl polyglycoside citrate or tartrate materials; or mono-, di- and tri-alkyl esters of citric acid and their metal salts.

Nonionic agents include condensation products of fatty acid esters, fatty alcohols, fatty acid amides or fatty-alkyl- or alkenyl-substituted phenols with ethylene and/or propylene oxide; fatty esters of polyhydric alcohol ethers, e.g. sorbitan fatty acid esters; condensation products of such esters with ethylene oxide, e.g. polyoxyethylene sorbitan fatty acid esters; alkyl glycosides, alkyl polyglycoside materials; block copolymers of ethylene oxide and propylene oxide; acetylenic glycols such as 2,4,7,9-tetramethyl-5-decyne-4,7-diol, ethoxylated acetylenic glycols; acrylic based graft copolymers; alkoxylated siloxane surfactants; or imidazoline type surfactants, e.g. 1-hydroxyethyl-2-alkylimidazoline.

Examples of a cationic surface-active agent include, for instance, an aliphatic mono-, di-, or polyamine as an acetate, naphthenate or oleate; an oxygen-containing amine such as an amine oxide, polyoxyethylene alkylamine or polyoxypropylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, an aerosol, a dispersion, an aqueous emulsion, a microemulsion, a dispersible concentrate, a dusting powder, a seed dressing, a fumigant, a smoke, a dispersible powder, an emulsifiable concentrate, granules or an impregnated strip. Moreover it can be in a suitable form for direct application or as a concentrate or primary composition which requires dilution with a suitable quantity of water or other diluent before application.

A dispersible concentrate comprises a compound of the invention dissolved in one or more water miscible or semi-water miscible solvents together with one or more surface active and/or polymeric material. Addition of the formulation to water results in the crystallisation of the active ingredient, the process being controlled by the surfactants and/or polymers resulting in a fine dispersion.

A dusting powder comprises a compound of the invention intimately mixed and ground with a solid pulverulent diluent, for example, kaolin.

An emulsifiable concentrate comprises a compound of the invention dissolved in a water-immiscible solvent which forms an emulsion or miscroemulsion on addition to water in the presence of an emulsifying agent.

A granular solid comprises a compound of the invention associated with similar diluents to those that may be employed in dusting powders, but the mixture is granulated by known methods. Alternatively it comprises the active ingredient absorbed or coated on a pre-formed granular carrier, for example, Fuller's earth, attapulgite, silica or limestone grit.

Wettable powders, granules or grains usually comprise the active ingredient in admixture with suitable surfactants and an inert powder diluent such as clay or diatomaceous earth.

Another suitable concentrate is a flowable suspension concentrate which is formed by grinding the compound with water or other liquid, surfactants and a suspending agent.

The concentration of the active ingredient in the composition of the present invention, as applied to plants is preferably within the range of 0.0001 to 1.0 percent by weight, especially 0.0001 to 0.01 percent by weight. In a primary composition, the amount of active ingredient can vary widely and can be, for example, from 5 to 95 percent by weight of the composition.

The invention is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth, as this is the time when the plant can be most severely damaged. The spray or dust can conveniently contain a pre- or post-emergence herbicide if this is thought necessary. Sometimes, it is practicable to treat the roots, bulbs, tubers or other vegetative propagule of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

In addition, the compounds of the invention can be applied to harvested fruits, vegetables or seeds to prevent infection during storage.

In addition, the compounds of the invention can be applied to plants or parts thereof which have been genetically modified to exhibit a trait such as fungal and/or herbicidal resistance.

In addition the compounds of the invention can be used to treat fungal infestations in timber and in public health applications.

Compounds of the invention may be prepared, in known manner, in a variety of ways. Such processes for the preparation of novel compounds of formula I constitute a feature of the invention.

Compounds of formula Ia, i.e. compounds of general formula I where Y is a formula (D) and L is —N(R$^5$)C(=X)NH—, can be prepared by reacting compounds of formula II or their hydrochloride salts, with compounds of formula III according to reaction scheme 1. A preferred base is triethylamine.

Scheme 1

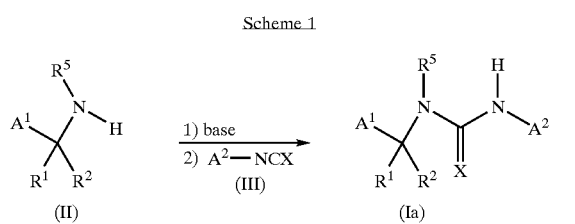

Compounds of formula Ib, i.e. compounds of general formula I where Y is of formula (D) and L is —N(R$^5$)C(=O)CH(R$^3$)—, may be prepared by reacting compounds of formula IV with compounds of formula II according to reaction scheme 2. A variety of methods are available to the chemist, for example, generation of the acid chloride of IV, using reagents such as phosphoryl chloride or oxalyl chloride, followed by addition of II. Alternatively, carbonyl diimidazole (CDI) can be used to activate compounds of formula IV prior to addition of II.

Scheme 2

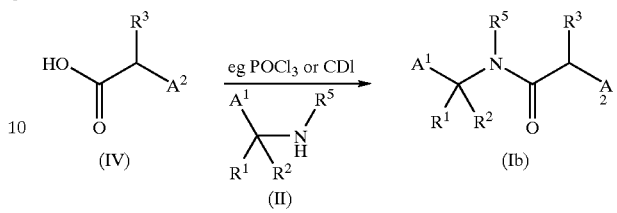

Compounds of formula Ic and Id, i.e. compounds of general formula I where Y is of formula (D) and L is —CH(R$^3$)—N(R$^5$)—W— and W is —C(=X)— or —CH(R$^4$)—, wherein R$^3$ is alkoxycarbonyl or carbamoyl respectively, can be prepared by various methods known to the skilled chemist. In particular, compounds of formula Ic or Id may be prepared from solid supported reagents of formula V according to reaction scheme 3, wherein the black circle represents Merrifield resin.

Scheme 3

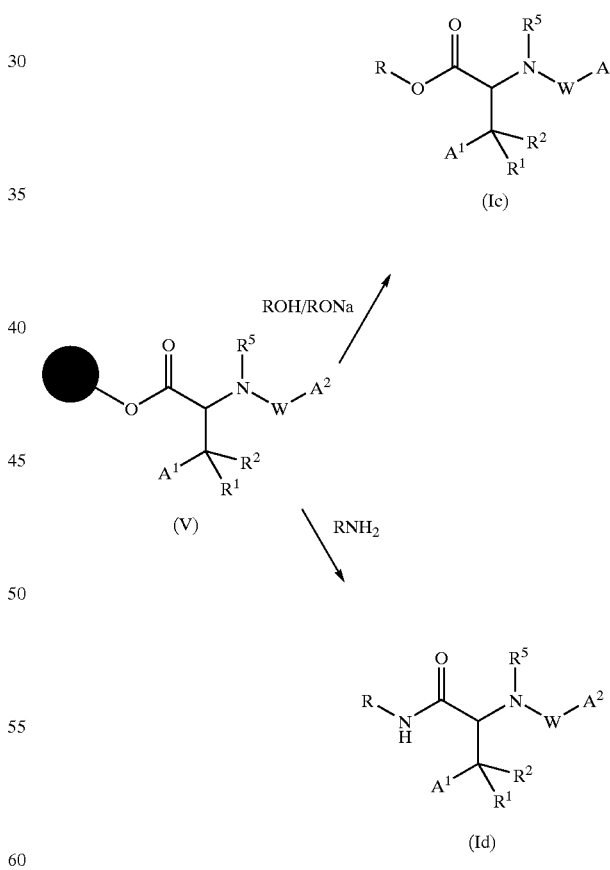

Compounds of formula Ie, i.e. compounds of general formula I where Y is of formula (D) and L is —CH(R$^3$)N(R$^5$)C(=X)— may be prepared by reacting compounds of formula VI with compounds of formula VII according to reaction scheme 4.

Scheme 4

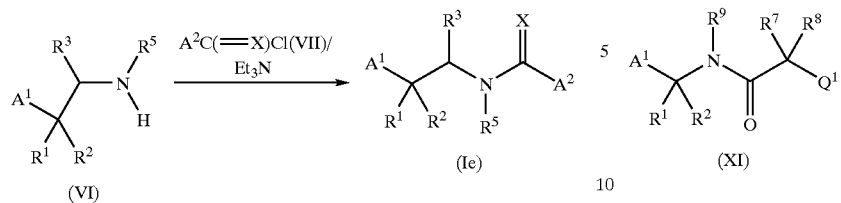

Compounds of formula If, i.e. compounds of general formula I where Y is of formula (B) and $L^1$ is —N($R^9$)C (=X)—$L^2$—, where $L^2$ is —CH($R^7$)CH($R^8$)—, —C($R^8$) ($R^7$)—$X^1$— or —C($R^7$)=C($R^8$)—, may be prepared according to Scheme 5 by reacting compounds of formula VIII or their hydrochloride salts with compounds of formula IX in the presence of a base, where $Q^1$ is a leaving group such as halogen, preferably chlorine. A preferred base is triethylamine. Compounds of formula IX can either be isolated or generated in situ.

Scheme 5

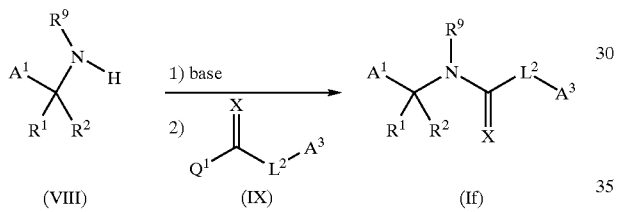

Compounds of formula Ig, i.e. compounds of general formula I where Y is of formula (E) and $L^1$ is —N($R^9$)C (=X)—NH—CH($R^7$)—, may be prepared according to Scheme 6 by reacting compounds of formula VIII or their hydrochloride salts with compounds of formula X. A preferred base is triethylamine.

Scheme 6

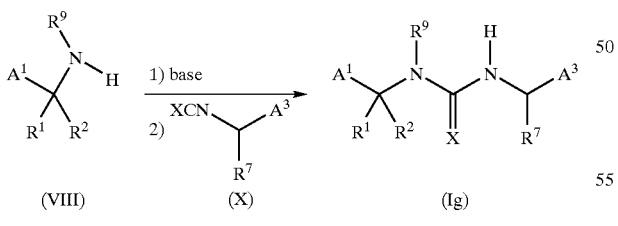

Compounds of formula Ih, i.e. compounds of general formula I where Y is of formula (E) and $L^1$ is —N($R^9$)C (=X)—C($R^7$)($R^8$)—$X^1$— wherein $R^7$ and $R^8$ are not both hydrogen and X is oxygen, may also be prepared according to Scheme 7 by reacting compounds of formula XI where $Q^1$ is a leaving group, preferably bromine, with $A^2$—$X^1$—H in the presence of a suitable base, preferably potassium tert-butoxide.

Scheme 7

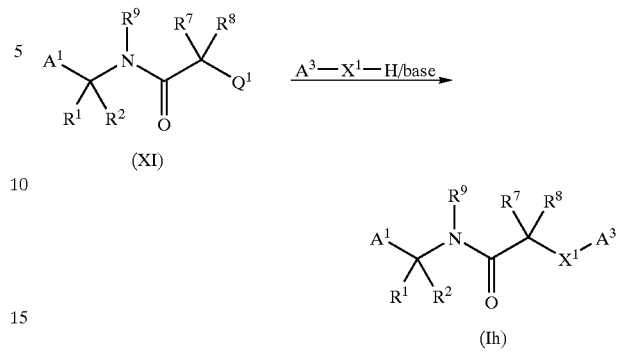

Compounds of formula Ii, i.e. compounds of general formula I where Y is of formula (E) and $L^1$ is —N($R^9$)C ($R^7$)=C($R^8$)—C(=X)— wherein $R^7$ is not hydrogen, may be prepared according to Scheme 8 by reacting compounds of formula VIII or their hydrochloride salts in the presence of a suitable base such as sodium acetate with compounds of formula XII.

Scheme 8

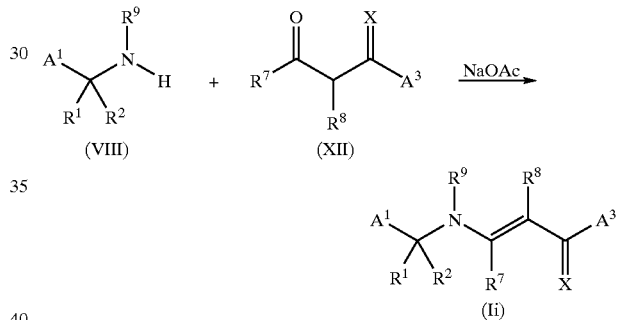

Compounds of formula Ij, i.e. compounds of general formula I where Y is of formula (E) and $L^1$ is —N($R^9$) CH=C($R^8$)—C(=X)—, may be prepared according to Scheme 9 by reacting compounds of formula VIII or their hydrochloride salts in the presence of a suitable base such as sodium acetate with compounds of formula XIII.

Scheme 9

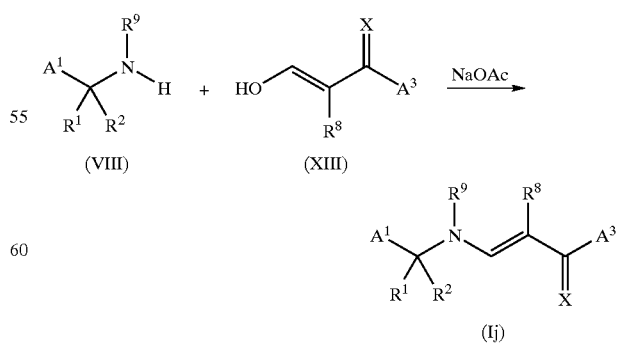

Compounds of formula Ik, i.e. compounds of general formula I where Y is of formula (E) and $L^1$ is —N($R^9$)C (=X)O—C(H)(R⁷)—, may be prepared according to Scheme 10 by reacting compounds of formula VIII or their hydrochloride salts in the presence of a suitable base such as triethylamine with compounds of formula XIV.

Scheme 10

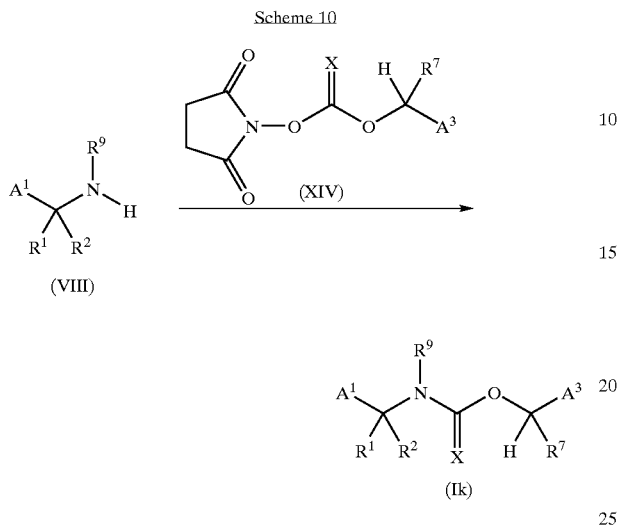

Collections of compounds of formula (I) may also be prepared in a parallel manner, either manually, automatically or semi-automatically. This parallel preparation may be applied to the reaction procedure, work-up or purification of products or intermediates. For a review of such procedures see by S. H. DeWitt in "Annual Reports in Combinatorial Chemistry and Molecular Diversity: Automated synthesis", Volume 1, Verlag Escom 1997, pages 69 to 77.

Furthermore, compounds of the formula (I) may be prepared using solid-supported methods, where the reactants are bound to a synthetic resin. See for example: Barry A. Bunin in "The Combinatorial Index", Academic Press, 1998 and "The tea-bag method" (Houghten, U.S. Pat. No. 4,631,211; Houghten et al., Proc. Natl. Acad. Sci. 1985, 82, 5131–5135).

The preparation of the processes described herein yields compounds of the formula (I) in the form of substance collections which are termed libraries. The present invention also relates to libraries which comprise at least two compounds of the formula (I).

Intermediates of formula V may be prepared in turn from compounds of formula XV, by methods analogous to that depicted in reaction scheme 11. Compounds of formula Va may be prepared by treating XV with a compound of formula XVI in the presence of a suitable base, such as triethylamine. Compounds of formula Vb may be prepared from compounds of formula XVa by treatment with compounds of formula XVII, sodium cyanoborohydride and acetic acid followed by reaction with compounds of formula XVIII and triethylamine.

Scheme 11

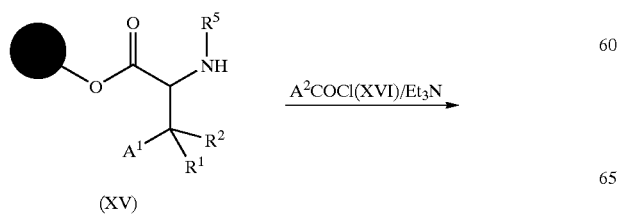

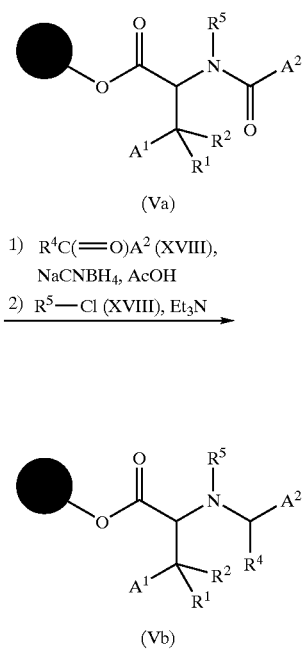

Compounds of formula XV can be prepared using similar methods to reaction scheme 12.

Scheme 12

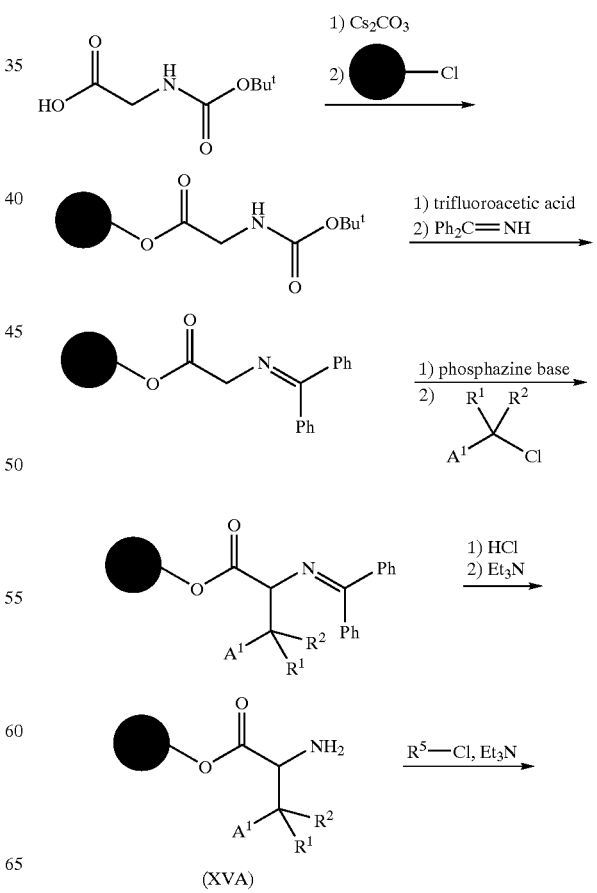

-continued

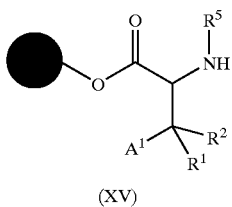

(XV)

Intermediates of formula VIII may be prepared by methods described in international application PCT/GB/99/00304.

Intermediates of formula IX can prepared from the corresponding carboxylic acid by methods known to the skilled chemist.

Intermediates of formula XI may be prepared according to Scheme 13 by reacting compounds of formula VIII in the presence of a suitable base such as triethylamine with compounds of formula XIX, in the presence of a carbonyl diimidazole (CDI).

Scheme 13

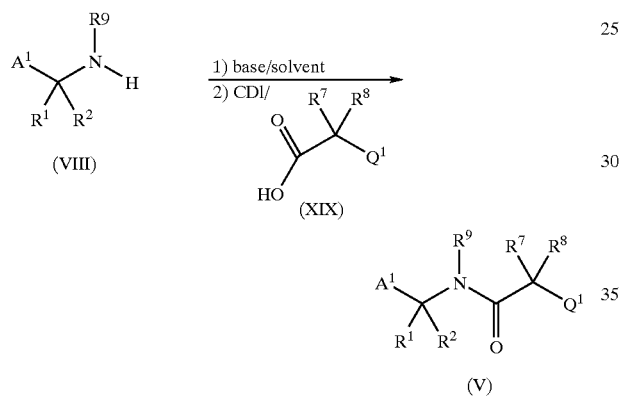

Other methods will be apparent to the chemist skilled in the art, as will be the methods for preparing starting materials and intermediates.

The invention is illustrated in the following Examples. Structures of isolated, novel compounds were confirmed by $^1$H NMR (in CDCl$_3$) and/or other appropriate analyses.

EXAMPLE 1

N-(2-Chlorophenyl)-N'-[(3-chloro-5-trifluoromethyl-2-pyridyl)methyl]thiourea (Compound 30)

To a suspension of (3-chloro-5-trifluoromethyl-2-pyridyl)methylamine hydrochloride (0.12 g) and 2-chlorophenylisothiocyanate (0.09 g) in dry tetrahydrofuran (10 ml) was added 10 drops of triethylamine. The mixture was stirred at room temperature overnight. The solvent was removed by evaporation in vacuo and the residue extracted with ethyl acetate and washed with 2M hydrochloric acid. The layers were separated and the organic phase was evaporated to dryness to give the title product, m.p. 126° C.

The following compounds of formula Im (see Table A), i.e. compounds of general formula I where Y is of formula (D) and A$^1$ is 3-Cl-5-CF$_3$-2-pyridyl, R$^1$ and R$^2$ are hydrogen and L is —NHC(=X)NH—, may be prepared by methods analogous to those of Example 1.

TABLE A

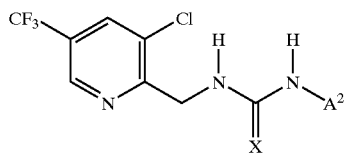

(Im)

| Cmp | X | A² | Characterising data |
|---|---|---|---|
| 1 | O | phenyl | m.p. 143–6° C. |
| 2 | S | phenyl | m.p. 151° C. |
| 3 | O | cyclohexyl | m.p. 135° C. |
| 4 | O | 2-Cl-phenyl | m.p. 125° C. |
| 5 | O | 2,3-diCl-phenyl | m.p. 142° C. |
| 6 | O | 3,5-diCl-phenyl | m.p. 81° C. |
| 7 | O | 4-Cl-phenyl | m.p. 180° C. |
| 8 | O | 2-CF₃-phenyl | m.p. 161° C. |
| 9 | O | 4-PhO-phenyl | m.p. 162° C. |
| 10 | O | 2,4-diCl-phenyl | m.p. 90° C. |
| 11 | O | 3,4-diMeO-phenyl | m.p. 179° C. |
| 12 | O | 2,6-xylyl | m.p. 175–7° C. |
| 13 | O | 2,6-diCl-phenyl | m.p. 178° C. |
| 14 | O | 3-tolyl | m.p. 165–7° C. |
| 15 | O | 3,4-diCl-phenyl | m.p. 132° C. |
| 16 | O | 3-CF₃-phenyl | $^1$H N.M.R δ(ppm) 4.7(2H, d), 6.7(1H, s), 7.2(1H, d), 7.3(1H, t), 7.5(1H, d), 7.6(1H, s), 7.85 (1H, s), 8.1(1H, s), 8.5(1H, s). |
| 17 | O | 3-MeO-phenyl | m.p. 118° C. |
| 18 | O | 4-CF₃-phenyl | m.p. 167–8° C. |
| 19 | O | 4-CN-phenyl | m.p. 209–13° C. |
| 20 | O | 2-MeO-phenyl | m.p. 144–6° C. |
| 21 | O | 4-MeO-phenyl | m.p. 192° C. |
| 22 | O | 2,4-diMeO-phenyl | m.p. 172° C. |
| 23 | O | 3-NO₂-phenyl | m.p. 94° C. |
| 24 | O | 2-NO₂-phenyl | m.p. 137–9° C. |
| 25 | O | 4-tolyl | m.p. 201° C. |
| 26 | O | 2-tolyl | m.p. 138° C. |
| 27 | O | 3-Br-phenyl | m.p. 104° C. |
| 28 | O | 4-Br-phenyl | m.p. 181–5° C. |
| 29 | S | cyclopropyl | m.p. 102° C. |
| 30 | S | 2-Cl-phenyl | m.p. 126° C. |
| 31 | S | 4-Cl-phenyl | m.p. 153° C. |
| 32 | S | 3,5-diCl-phenyl | m.p. 179° C. |
| 33 | S | 2,4-diCl-phenyl | m.p. 160° C. |
| 34 | S | 2,3-diCl-phenyl | m.p. 170–2° C. |
| 35 | S | 2-CF₃-phenyl | m.p. 140–2° C. |
| 36 | S | 2,6-xylyl | m.p. 170–3° C. |
| 37 | S | 3,4-diMeO-phenyl | m.p. 172–5° C. |
| 38 | S | 3-PhO-phenyl | m.p. 152–3° C. |
| 39 | S | (structure) | oil |
| 40 | S | 3-MeS-phenyl | m.p. 142–3° C. |
| 41 | S | 3-acetylphenyl | m.p. 160° C. |
| 42 | S | 3-Cl-4-tolyl | m.p. 163° C. |
| 43 | S | 3-(PhSO₂)-phenyl | m.p. 195–8° C. |
| 44 | S | 4-But-phenyl | m.p. 108–9° C. |
| 45 | S | 3-CF₃-phenyl | m.p. 158–60° C. |
| 46 | S | 4-NMe₂-phenyl | m.p. 177–81° C. |
| 47 | S | 4-MeSO₂-phenyl | m.p. 160–3° C. |
| 48 | S | 4-MeS-phenyl | m.p. 172–6° C. |
| 49 | S | 6-NO₂-2-naphthyl | m.p. 194–8° C. |
| 50 | S | 2-tolyl | m.p. 158–60° C. |
| 51 | S | 2-Pr$^i$-phenyl | m.p. 124–7° C. |
| 52 | S | 2,6-diCl-phenyl | m.p. 186–9° C. |
| 53 | S | 4-Br-phenyl | m.p. 143–5° C. |
| 54 | S | 2-Cl-4-MeSO₂-phenyl | m.p. 176–8° C. |
| 55 | S | 4-Me-2-NO₂-phenyl | m.p. 136–9° C. |
| 56 | S | 2-Cl-4-PrSO₂-phenyl | m.p. 166–9° C. |

TABLE A-continued (Im)

structure: CF$_3$-pyridyl (with Cl) -CH$_2$-NH-C(=X)-NH-A$^2$

| Cmp | X | A$^2$ | Characterising data |
|---|---|---|---|
| 57 | S | 4-(4-Me-benzylsulfonyl)phenyl | m.p. 185–9° C. |
| 58 | S | 4-(4-Cl-phenylthio)phenyl | m.p. 147–50° C. |
| 59 | S | cyclohexyl | $^1$H N.M.R δ(ppm) 1.1–2.1(10H, m), 3.8(1H, br), 5.0(2H, br), 6.5(1H, br), 7.4(1H, br), 8.0(1H, s) and 8.7(1H, s) |
| 60 | S | 4-PhO-phenyl | m.p. 109–10° C. |
| 61 | S | 2-PhO-phenyl | $^1$H N.M.R δ(ppm) 8.63(1H, s), 8.1(2H, d), 7.95(1H, s), 7.65(1H, s), 7.65 (1H, d), 7.4–6.9(8H, m) and 5.1(2H, d). |
| 62 | S | 3-Pr$^i$O-phenyl | $^1$H N.M.R δ(ppm) 8.6(1H, s), 8.18(1H, s), 8.04(1H, br), 7.95(1H, s), 7.35 (1H, t), 6.86(3H, d), 5.1(2H, d), 4.58(1H, m), 1.35(6H, d) |
| 63 | S | 3,4-diCl-phenyl | $^1$H N.M.R δ(ppm) 8.6(1H, s), 8.0(1H, s), 7.5–7.1(3H, m), 4.9(2H, d), 4.7(2H, d) |
| 64 | S | 2-MeO-phenyl | $^1$H N.M.R δ(ppm) 8.64(1H, s), 8.05 (1H, br), 7.9(1H, s), 7.85(1H, br), 7.5 (1H, d), 7.25(1H, dd), 7.0(2H, dd), 5.1(2H, d), 3.85(3H, s) |

EXAMPLE 2

N-[(3-Chloro-5-trifluoromethyl-2-pyridyl)methyl]-2-nitrophenylacetamide (Compound 108)

To a stirred suspension of 2-nitrophenylacetic acid (0.36 g) in dry toluene (5 ml) at room temperature was added phosphoryl chloride (0.37 g) and stirring was continued overnight. Meanwhile a solution of the amine was prepared, (3-Chloro-5-trifluoromethyl-2-pyridyl)methylamine hydrochloride (0.49 g) in dry toluene (5 ml) and triethylamine (1.23 g) was stirred at room temperature for 1 hour and then filtered. The solid was washed with dry toluene and the combined filtrates were added dropwise to the above suspension of acid chloride with ice-cooling. After addition, the mixture was stirred at room temperature overnight. Dichloromethane was added and the mixture was washed with water. The aqueous layer was separated and back-extracted with dichloromethane. The combined organic extracts were washed with saturated sodium bicarbonate solution, then brine, then dried (MgSO$_4$), and the solvent removed. The resulting residue was purified by silica gel chromatography eluting with ethyl acetate/light petroleum (b.p. 40–60° C.) to give the title product, m.p. 123–4° C.

The following compounds of formula In (see Table B), i.e. compounds of general formula I where Y is of formula (D) and A$^1$ is 3-Cl-5-CF$_3$-2-pyridyl, R$^1$ and R$^2$ are hydrogen and L is —NHC(=O)CH(R$^3$)—, may be prepared by methods analogous to those of Example 2.

TABLE B (In)

structure: CF$_3$-pyridyl (with Cl) -CH$_2$-NH-C(=X)-CH(R$^3$)-A$^2$

| Cmp | R$^3$ | A$^2$ | m.p. (° C.) |
|---|---|---|---|
| 101 | H | thienyl | oil |
| 102 | ethyl | phenyl | oil |
| 103 | MeC(=O)O— | phenyl | oil |
| 104 | H | 2,4-diMeO-phenyl | oil |
| 105 | phenyl | phenyl | oil |
| 106 | Cl | phenyl | 102–3 |
| 107 | H | 2,6-diCl-phenyl | 136–9 |
| 108 | H | 2-NO$_2$-phenyl | 123–4 |
| 109 | H | 3-Cl-phenyl | 88–9 |
| 110 | H | 2-Cl-6-F-phenyl | 133–4 |
| 111 | Pr$^i$ | i-imidazolyl | 120 |
| 112 | H | (N-methyl-ethoxy-pyrrolinone) | 134 |

The $^1$H N.M.R. data of those compounds in Table B which were not solid at room temperature are presented below.

Compound 101
$^1$H N.M.R. (CDCl$_3$) δ(ppm) 3.9 (2H, s), 4.7 (2H, d), 7.0 (2H, d), 7.1 (1H, br.s), 7.3 (2H, m), 7.9 (1H, s) and 8.7 (1H, s);

Compound 102
$^1$H N.M.R. (CDCl$_3$) δ(ppm) 0.9 (3H, t), 1.9 (1H, m), 2.25 (1H, m), 3.4 (1H, t), 4.7 (2H, qd), 6.9 (1H, bs), 7.2–7.4 (5H, m), 7.9 (1H, s), 8.65 (1H, s);

Compound 103
$^1$H N.M.R. (CDCl$_3$) δ(ppm) 2.25 (3H, s), 4.75 (2H, d), 6.2 (1H, s), 7.4 (3H, m), 7.5 (2H, m), 7.7 (1H, bs), 8.0 (1H, s), 8.75 (1H, s);

Compound 104
$^1$H N.M.R. (CDCl$_3$) δ(ppm) 3.65 (2H, s), 3.8 (3H, s), 3.9 (3H, s), 4.7 (2H, d), 6.8–7.0 (3H, m), 7.1 (1H, bs), 7.9 (1H, s), 8.75 (1H, s); and Compound 105
$^1$H N.M.R. (CDCl$_3$) δ(ppm) 4.8 (2H, d), 5.1 (1H, s), 7.1–7.4 (1H, m), 7.9 (1H, s) and 8.65 (1H, s).

EXAMPLE 3

Methyl 2-[(2-chlorobenzyl)amino]-3-[3-chloro-5-(trifluoromethyl)-2-pyridyl]propanoate (Compound 218)

To a mixture of the product from stage h) below in tetrahydrofuran (12 ml) and methanol (4 ml) was added 1M sodium methoxide in methanol (4 drops) and the mixture was heated at 65° C. for 3 days. The mixture was filtered and the solid washed successively with portions (5 ml) of methanol, dichloromethane and methanol. The combined filtrates were evaporated to give the title product. $^1$H N.M.R. δ(ppm) 8.63 (1H, s), 7.89 (1H, s), 7.15–7.35 (4H, m), 3.92 (3H, m), 3.74 (3H, s), 3.42 (2H, d).

Preparation of Starting Materials
N-(tert-Butoxycarbonyl)glycine cesium salt

To a mixture of N-(tert-butoxycarbonyl)glycine (42.0 g) in water (250 ml) was added cesium carbonate (39.1 g). The mixture was stirred at room temperature for 10 minutes. The water was removed by azeotropic distillation with toluene to give the title product.

Attachment to Solid Support

Merrifield resin (61.2 g) was swollen in dry dimethylformamide (350 ml). The product from stage a) (75.5 g) was added followed by more dry dimethylformamide (250 ml) and the mixture was stirred at 65° C. overnight. On cooling, the mixture was filtered and the solid washed successively with portions (400 ml) of dimethylformamide, dimethylformamide/water (1:1), water, dichloromethane, methanol, dichloromethane and finally methanol (×2). The solid was dried in a vacuum oven overnight.

Treatment with Trifluoroacetic Acid

To a mixture of the product from stage b) (76.2 g) swollen in dry dichloromethane (660 ml) was added trifluoroacetic acid (220 ml) and the mixture was stirred at room temperature for 5.5 hours. The mixture was filtered and the solid was washed successively with portions (400 ml) of dichloromethane (×2), methanol, dichloromethane and methanol (×2). The resin was dried overnight.

Treatment with Benzophenone Imine

To a mixture of the product from stage c) (76.6 g) swollen in dry dichloromethane (650 ml) was added benzophenone imine (61 ml) in dichloromethane (100 ml) and the mixture stirred overnight. The mixture was filtered and the solid was successively washed with portions (400 ml) of dichloromethane, 20% aqueous tetrahydrofuran (×2), tetrahydrofuran, dichloromethane, methanol, dichloromethane and methanol (×2). The solid was dried in a vacuum oven overnight.

Electrophilic Substitution of the Imine

To a mixture of the product from stage d) (40.4 g) swollen in N-methylpyrrolidinone (250 ml) was added phosphazine base P(1)-tert-Bu-tris(tetramethylene) (38 ml). 3-Chloro-2-chloromethyl-5-trifluoromethylpyridine (42.4 g) was then added and the mixture was stirred at room temperature overnight. The mixture was filtered and the solid was washed successively with portions (200 ml) of N-methylpyrrolidinone (×2), dichloromethane (×2) methanol, dichloromethane and methanol (×2). The solid was dried in a vacuum oven overnight.

Conversion of Imine to Amine Hydrochloride

To a mixture of the product from stage e) (52.1 g) swollen in tetrahydrofuran (750 ml) was added 2M hydrochloric acid (250 ml). The mixture was stirred for 4 hours and then filtered. The solid was washed successively with portions (250 ml) of tetrahydrofuran (×2), dichloromethane (×2), methanol, dichloromethane, methanol and diethyl ether. The solid was dried in a vacuum oven overnight.

Conversion to Amine

A mixture of the product from stage f) in 10% triethylamine in dichloromethane was stirred at room temperature for 2 hours. The mixture was filtered and the solid was stirred in 5% triethylamine in dichloromethane for 1 hour. The mixture was filtered again, and the solid was stirred in dichloromethane for 1 hour. The mixture was filtered and the solid washed successively with portions of methanol, dichloromethane, methanol and diethyl ether (×2). The solid was dried in a vacuum oven overnight.

Conversion of Primary Amine to Secondary Amine

A mixture of the product from stage g) (4.2 mmol) in trimethylorthoformate (90 ml) was treated with 2-chlorobenzaldehyde (42 mmol) and stirred at room temperature for 6 hours. Sodium cyanoborohydride (42 mmol) followed by acetic acid (1.3 ml) was then added and the mixture stirred at room temperature for 16 hours. The mixture was filtered and the solid was washed successively with portions of aqueous tetrahydrofuran, tetrahydrofuran, methanol, dichloromethane, methanol, dichloromethane, methanol and diethyl ether (×2). The solid was dried in a vacuum oven overnight.

The following compounds of formula Ip (see Table C), i.e. compounds of general formula I where Y is of formula (D) and $A^1$ is 3-Cl-5-$CF_3$-2-pyridyl, $R^1$ and $R^2$ are hydrogen and L is —CH($R^3$)N($R^5$)$CH_2$—, may be prepared by methods analogous to those of Example 3.

TABLE C (Ip)

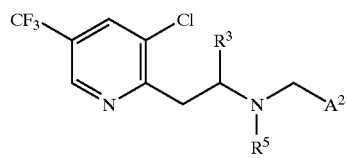

| Cmp | $R^3$ | $R^5$ | $A^2$ | Characterising data |
|---|---|---|---|---|
| 201 | EtNHC(=O)— | H | phenyl | $^1$H N.M.R δ(ppm)8.61(1H, s), 7.8 (1H, s), 7.43(1H, m), 7.1–7.3(5H, m), 3.1–3.3(7H, m), 1.16(3H, t) |
| 202 | EtNHC(=O)— | MeC(=O)— | phenyl | $^1$H N.M.R δ(ppm)8.64(1H, s), 7.73 (1H, s), 7.27(3H, m), 7.10(2H, m), 6.53(1H, m), 5.82(1H, t), 4.70(2H, m), 3.43(2H, m), 3.20(2H, m), 2.14 (3H, s) and 1.03(3H, t). |
| 203 | EtNHC(=O)— | H | 3-tolyl | $^1$H N.M.R δ(ppm)8.63(1H, s), 7.86 (1H, s), 7.54(1H, m), 7.13(1H, m), 7.06(1H, m), 6.98(2H, m), 3.1–3.8 (7H, m), 2.34(3H, s), 1.17(3H, t) |

TABLE C-continued (Ip)

| Cmp | R³ | R⁵ | A² | Characterising data |
|---|---|---|---|---|
| 204 | MeOC(=O)— | H | 3-tolyl | m/z(ES)387(M+H)⁻ |
| 205 | EtOC(=O)— | H | 3-tolyl | ¹H N.M.R δ(ppm)8.67(1H, s), 7.88 (1H, s), 7.18(1H, m), 7.02(2H, m), 4.10(2H, q), 3.78(3H, m), 3.37(2H, m), 2.32(3H, s), 1.24(3H, t) |
| 206 | EtNHC(=O)— | H | 4-MeO-phenyl | m/z(ES)416(M+H)⁻ |
| 207 | EtNHC(=O)— | H | 2-Cl-phenyl | m/z(ES)420(M+H)⁻ |
| 208 | EtNHC(=O)— | H | 2,5-diF-phenyl | m/z(ES)422(M+H)⁻ |
| 209 | EtNHC(=O)— | H | 2-NO₂-phenyl | m/z(ES)431(M+H)⁻ |
| 210 | EtNHC(=O)— | H | 2-naphthyl | m/z(ES)436(M+H)⁻ |
| 211 | EtNHC(=O)— | H | 3,4-diMeO-phenyl | m/z(ES)446(M+H)⁻ |
| 212 | EtNHC(=O)— | H | 2-CF₃-phenyl | m/z(ES)454(M+H)⁻ |
| 213 | EtNHC(=O)— | H | 2,4-diCl-phenyl | m/z(ES)454(M+H)⁻ |
| 214 | EtNHC(=O)— | H | 3-PhO-phenyl | m/z(ES)478(M+H)⁻ |
| 215 | MeNHC(=O)— | H | 2-Cl-phenyl | m/z(ES)406(M+H)⁻ |
| 216 | MeNHC(=O)— | H | 3-NO₂-phenyl | m/z(ES)417(M+H)⁻ |
| 217 | MeOC(=O)— | H | 4-MeO-phenyl | m/z(ES)403(M+H)⁻ |
| 218 | MeOC(=O)— | H | 2-Cl-phenyl | ¹H N.M.R δ(ppm)8.63(1H, s), 7.89 (1H, s), 7.15–7.35(4H, m), 3.92(3H, m), 3.74(3H, s), 3.42(2H, d) |
| 219 | MeOC(=O)— | H | 2,6-diF-phenyl | ¹H N.M.R δ(ppm)8.62(1H, s), 7.83 (1H, s), 7.20(1H, m), 6.34(2H, m), 3.73(3H, m), 3.68(3H, s), 3.28(2H, d) |
| 220 | MeOC(=O)— | H | 2-NO₂-phenyl | m/z(ES)418(M+H)⁻ |
| 221 | MeOC(=O)— | H | 2-naphthyl | m/z(ES)423(M+H)⁻ |
| 222 | MeOC(=O)— | H | 3,4-diMeO-phenyl | m/z(ES)433(M+H)⁻ |
| 223 | MeOC(=O)— | H | 2-CF₃-phenyl | m/z(ES)441(M+H)⁻ |
| 224 | MeOC(=O)— | H | 2,6-diCl-phenyl | ¹H N.M.R δ(ppm)8.62(1H, s), 7.89 (1H, s), 7.1–7.35(3H, m), 3.83(3H, m), 3.72(3H, s), 3.39(2H, m) |
| 225 | MeOC(=O)— | H | 3-PhO-phenyl | ¹H N.M.R δ(ppm)8.62(1H, s), 7.83 (1H, s), 6.3–7.2(9H, m), 3.79(3H, m), 3.71(3H, s), 3.38(2H, m) |
| 226 | EtOC(=O)— | H | phenyl | ¹H N.M.R δ(ppm)8.62(1H, s), 7.88 (1H, s), 7.1–7.3(5H, m), 4.18(2H, q), 3.79(3H, m), 3.38(2H, m), 1.21(3H, t) |
| 227 | EtOC(=O)— | H | 4-MeO-phenyl | ¹H N.M.R δ(ppm)8.63(1H, s), 7.88 (1H, s), 7.12(2H, d), 6.79(2H, d), 4.10(2H, q), 3.81(3H, s), 3.73(3H, m), 3.38(2H, m), 1.23(3H, t) |
| 228 | EtOC(=O)— | H | 2-Cl-phenyl | ¹H N.M.R δ(ppm)8.62(1H, s), 7.86 (1H, s), 7.1–7.4(4H, m), 4.19(2H, q), 3.89(3H, m), 3.40(2H, m), 1.23(3H, t) |
| 229 | EtOC(=O)— | H | 2,6-diF-phenyl | ¹H N.M.R δ(ppm)8.61(1H, s), 7.82 (1H, s), 7.21(1H, m), 6.82(2H, t), 4.16(2H, q), 3.91(3H, m), 3.38(2H, d), 1.22(3H, t) |
| 230 | EtOC(=O)— | H | 2-NO₂-phenyl | ¹H N.M.R δ(ppm)8.62(1H, s), 7.87 (2H, m), 7.35–7.55(3H, m)4.20(2H, m), 4.08(2H, m), 3.36(m), 3.37(2H, m), 1.14(3H, t) |
| 231 | EtOC(=O)— | H | 2-naphthyl | ¹H N.M.R δ(ppm)8.61(1H, s), 7.25–7.9(8H, m), 3.8–4.3(5H, m), 3.41(2H, m), 1.24(3H, t) |
| 232 | EtOC(=O)— | H | 3,4-diMeO-phenyl | ¹H N.M.R δ(ppm)8.64(1H, s), 7.89 (1H, s), 6.78(3H, m), 4.19(2H, q), 3.86(3H, s), 3.81(3H, s), 3.75(2H, m), 3.39(2H, m), 1.24(3H, t) |
| 233 | EtOC(=O)— | H | 2-CF₃-phenyl | ¹H N.M.R δ(ppm)8.66(1H, s), 7.91 (1H, s), 7.3–7.65(4H, m), 4.21(2H, m), 3.98(3H, m), 3.41(3H, m), 1.26 (3H, t) |

TABLE C-continued

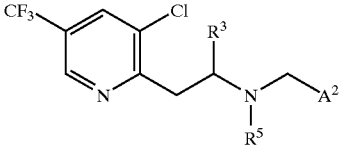

(Ip)

| Cmp | R³ | R⁵ | A² | Characterising data |
|---|---|---|---|---|
| 234 | EtOC(=O)— | H | 2,4-diCl-phenyl | ¹H N.M.R δ(ppm)8.64(1H, s), 7.89 (1H, s), 7.1–7.35(3H, m), 4.20(2H, m), 3.86(3H, m), 3.40(2H, m), 1.24 (3H, t) |
| 235 | EtOC(=O)— | H | 3-PhO-phenyl | ¹H N.M.R δ(ppm)8.62(1H, s), 7.83 (1H, s), 6.8–7.4(9H, m), 4.18(2H, q), 3.77(3H, m), 3.38(2H, m), 1.22(3H, t) |
| 236 | MeNHC(=O)— | H | 2-naphthyl | m/z(ES)422(M+H)⁻ |
| 237 | MeNHC(=O)— | H | 2,4-diCl-phenyl | m/z(ES)440(M+H)⁻ |
| 238 | MeNHC(=O)— | H | 3-PhO-phenyl | m/z(ES)464(M+H)⁻ |
| 239 | MeOC(=O)— | H | phenyl | m/z(ES)373(M+H)⁻ |

EXAMPLE 4

Methyl 2-bromobenzoylamino-3-(3-chloro-5-trifluoromethyl-2-pyridyl)propionate
(Compound 321)

To a mixture of the product from Example 3 stage g) in dry dichloromethane was added triethylamine and the solution was stirred for 15 minutes. 2-Bromobenzoyl chloride in dry dichloromethane was added, and the mixture was stirred at room temperature overnight. The mixture was filtered and the solid was washed successively with portions (125 ml) of dichloromethane (×2), methanol, dichloromethane, methanol, dichloromethane (×2), methanol and diethyl ether (×2). The solid was dried in a vacuum oven overnight. To this solid in tetrahydrofuran (12 ml) and methanol (4 ml) was added 1M sodium methoxide in methanol (4 drops) and the mixture was heated at 65° C. for 3 days. The mixture was filtered and the solid washed successively with portions (5 ml) of methanol, dichloromethane and methanol. The combined filtrates were evaporated to give the title product. ¹H N.M.R. δ(ppm) 8.62 (s), 7.31 (s), 7.56 (2H, m), 7.37 (m), 7.29 (m), 5.40 (m), 3.76 (3H, s) and 3.71 (2H, m).

The following compounds of formula Iq (see Table D); i.e. compounds of general formula I where Y is of formula (D) and A¹ is 3-Cl-5-CF₃-2-pyridyl, R¹ and R² are hydrogen and L is —CH(R³)NHC(=O)—, may be prepared by methods analogous to those of Example 4.

TABLE D

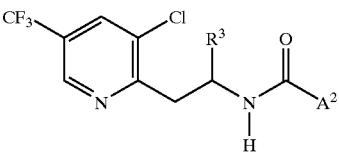

(Iq)

| Cmp | R³ | A² | Characterising data |
|---|---|---|---|
| 301 | EtNHC(=O)— | 4-MeO-phenyl | ¹H N.M.R δ(ppm)8.66(1H, s), 7.91(1H, s), 7.89(1H, d), 7.77(2H, d), 6.94(2H, d), 6.32(1H, d), 6.32(1H, d), 5.21(1H, m), 3.97(3H, s), 3.55(2H, m), 3.25(2H, m), 1.08(3H, t) |
| 302 | EtNHC(=O)— | 2,6-diCl-phenyl | ¹H N.M.R δ(ppm)8.60(1H, s), 7.91(1H, s), 7.2–7.4(3H, m), 6.74(1H, m), 5.33(1H, m), 3.62(2H, m), 3.29(2H, m), 1.12(3H, t) |
| 303 | EtNHC(=O)— | cyclopropyl | m/z(ES)364(M+H)⁻ |
| 304 | EtNHC(=O)— | phenyl | m/z(ES)400(M+H)⁻ |
| 305 | EtNHC(=O)— | cyclohexyl | m/z(ES)406(M+H)⁻ |
| 306 | EtNHC(=O)— | 4-Cl-phenyl | m/z(ES)435(M+H)⁻ |
| 307 | EtNHC(=O)— | 3-NO₂-phenyl | m/z(ES)445(M+H)⁻ |
| 308 | EtNHC(=O)— | 3-CF₃-phenyl | m/z(ES)468(M+H)⁻ |
| 309 | EtNHC(=O)— | 4-PhO-phenyl | m/z(ES)476(M+H)⁻ |
| 310 | EtNHC(=O)— | 2-Br-phenyl | m/z(ES)478(M+H)⁻ |
| 311 | MeNHC(=O)— | cyclopropyl | ¹H N.M.R δ(ppm)8.67(1H, s), 7.92(1H, s), 6.70(1H, br), 5.09(1H, m), 3.46(2H, m), 2.80(3H, m), 1.42(1H, m), 0.97(2H, m), 0.81(2H, m) |

TABLE D-continued (Iq)

| Cmp | R³ | A² | Characterising data |
|---|---|---|---|
| 312 | MeNHC(=O)— | cyclohexyl | ¹H N.M.R δ(ppm)8.64(1H, s), 7.91(1H, s), 7.08(1H, d), 6.68(1H, m), 5.04(1H, q), 3.43(2H, m), 2.73(3H, m), 1.2–2.3(11H, m) |
| 313 | MeNHC(=O)— | 2,6-diCl-phenyl | ¹H N.M.R δ(ppm)8.62(1H, s), 7.85(1H, s), 7.46(1H, d), 7.34(3H, m), 4.82(1H, m), 5.36(1H, m), 3.62(2H, m), 2.84(3H, d) |
| 314 | MeNHC(=O)— | phenyl | m/z(ES)386(M+H)⁻ |
| 315 | MeNHC(=O)— | 4-MeO-phenyl | m/z(ES)416(M+H)⁻ |
| 316 | MeNHC(=O)— | 4-biphenylyl | m/z(ES)462(M+H)⁻ |
| 317 | MeOC(=O)— | phenyl | ¹H N.M.R δ(ppm)8.95(1H, s), 7.93(2H, m), 7.26(3H, m), 5.38(1H, m), 3.76(3H, s), 3.70(2H, m) |
| 318 | MeOC(=O)— | cyclohexyl | ¹H N.M.R δ(ppm)8.66(1H, s), 7.91(1H, s), 6.63(1H, d), 5.18(1H, m), 3.71(3H, s), 3.57(2H, m), 1.2–2.15(11H, m) |
| 319 | MeOC(=O)— | 2,6-diCl-phenyl | ¹H N.M.R δ(ppm)8.60(1H, s), 7.95(1H, s), 7.28(3H, m), 1.30(1H, d), 5.42(2H, m), 3.74(5H, m) |
| 320 | MeOC(=O)— | 4-biphenylyl | ¹H N.M.R δ(ppm)8.72(1H, s), 7.92(1H, s), 7.35–7.9(9H, m), 5.39(1H, m), 3.78(3H, s), 3.70(2H, m) |
| 321 | MeOC(=O)— | 2-Br-phenyl | ¹H N.M.R δ(ppm)8.62(1H, s), 7.31(1H, s), 7.56(2H, m), 7.37(1H, m), 7.29(1H, m), 5.40(1H, m), 3.76(3H, s), 3.71(2H, m) |
| 322 | EtOC(=O)— | cyclohexyl | ¹H N.M.R δ(ppm)8.64(1H, s), 7.92(1H, s), 6.64(1H, d), 5.16(1H, m), 4.18(2H, m), 3.59(2H, m), 0.3–2.2(11H, m), 1.22(3H, t) |
| 323 | EtOC(=O)— | 4-MeO-phenyl | ¹H N.M.R δ(ppm)8.69(1H, s), 7.91(1H, s), 7.77(2H, d), 7.38(1H, d), 8.92(2H, d), 5.32(1H, m), 4.20(2H, m), 3.34(3H, t), 3.67(2H, m) |
| 324 | EtOC(=O)— | 3-CF₃-phenyl | ¹H N.M.R δ(ppm)8.68(1H, s), 8.06(1H, s), 7.96(2H, m), 7.30(2H, m), 7.60(2H, m), 5.36(1H, m), 4.21(2H, m), 3.71(2H, m), 1.23(3H, t). |
| 325 | EtOC(=O)— | 2,6-diCl-phenyl | ¹H N.M.R δ(ppm)8.62(1H, s), 7.94(1H, s), 7.26(3H, m), 7.04(1H, d), 5.41(1H, m), 4.21(2H, m), 3.73(2H, m), 1.22(3H, t) |
| 326 | EtOC(=O)— | 2-Br-phenyl | ¹H N.M.R δ(ppm)8.64(1H, s), 7.93(1H, s), 7.57(1H, m), 7.33(1H, m), 7.26(1H, m), 5.39(1H, m), 4.22(2H, m), 3.75(2H, m), 1.23(3H, t) |
| 327 | MeOC(=O)— | cyclopropyl | m/z(ES)351(M+H)⁻ |
| 328 | MeOC(=O)— | 4-MeO-phenyl | m/z(ES)417(M+H)⁻ |
| 329 | MeOC(=O)— | 4-Cl-phenyl | m/z(ES)421(M+H)⁻ |
| 330 | MeOC(=O)— | 3-NO₂-phenyl | m/z(ES)432(M+H)⁻ |
| 331 | MeOC(=O)— | 3-CF₃-phenyl | m/z(ES)455(M+H)⁻ |
| 332 | EtOC(=O)— | cyclopropyl | m/z(ES)365(M+H)⁻ |
| 333 | EtOC(=O)— | phenyl | m/z(ES)401(M+H)⁻ |
| 334 | EtOC(=O)— | 4-Cl-phenyl | m/z(ES)435(M+H)⁻ |
| 335 | EtOC(=O)— | 3-NO₂-phenyl | m/z(ES)446(M+H)⁻ |
| 336 | EtOC(=O)— | 4-biphenylyl | m/z(ES)477(M+H)⁻ |
| 337 | MeNHC(=O)— | 4-Cl-phenyl | m/z(ES)420(M+H)⁻ |
| 338 | MeNHC(=O)— | 3-NO₂-phenyl | m/z(ES)431(M+H)⁻ |
| 339 | MeNHC(=O)— | 3-CF₃-phenyl | m/z(ES)454(M+H)⁻ |
| 340 | MeNHC(=O)— | 2-Br-phenyl | m/z(ES)464(M+H)⁻ |

EXAMPLE 5

N-[2-(3-Chloro-5-trifluoromethyl-2-pyridyl)ethyl]-2,6-dichlorobenzamide (Compound 401)

To a suspension of 2-(3-chloro-5-trifluoromethyl-2-pyridyl)ethylammonium chloride (0.2 g) in dry dichloromethane at 10° C. was added 2,6-dichlorobenzoyl chloride (0.13 ml) followed by dropwise addition of dry triethylamine (0.3 ml). The mixture was warmed with stirring to 22° C. over 18 hours. The mixture was evaporated on to flash silica. Chromatography over silica eluting with 20–50% diethyl ether in light petroleum (b.p. 40–60° C.) gave the title product, m.p. 103–5° C.

Preparation of Starting Material
2-(3-Chloro-5-trifluoromethyl-2-pyridyl)ethylammonium chloride To a solution of the product from Example 6 (1.0 g) in ethanol (10 ml) was added hydrazine hydrate (0.15 ml) and the mixture was heated under reflux for 3 hours. Concentrated hydrochloric acid (1 ml) was added and the mixture was heated at 80° C. for 1 hour to give a filterable precipitate. The mixture was cooled to 10° C., filtered and then evaporated to dryness in vacuo. The residue was dissolved in water (10 ml) and then basified to greater than pH 10 using 2M aqueous sodium hydroxide solution. The aqueous solution was ether extracted (3×15 ml) and the combined extracts were brine washed (2×10 ml). The organic extract was dried (MgSO$_4$), the filtrate acidified with 6M hydrogen chloride in diethyl ether (5 ml) and evaporated to dryness. The solid residue was triturated with ethyl ether, filtered and dried in vacuo to give the title compound, m.p. 188–92° C.

EXAMPLE 6

2-{2-[3-Chloro-5-(trifluoromethyl)-2-pyridyl]ethyl}-1,3-isoindolinedione (Compound 402)

To a solution of the product from Example 7 (5.63 g) in glacial acetic acid (50 ml) was added 48% hydrogen bromide solution (10 ml) and the mixture was heated at 120° C. for 2 hours. The cold mixture was evaporated in vacuo and partitioned between water (100 ml) and dichloromethane (100 ml). The aqueous layer was separated and extracted with dichloromethane (2×10 ml). The combined extracts were water washed (2×20 ml), dried (MgSO$_4$), and evaporated onto flash silica. Chromatography over silica eluting with 3–30% diethyl ether in light petroleum (b.p. 40–60° C.) gave the title compound, m.p. 147–8° C.

EXAMPLE 7

Diethyl 2-[3-chloro-5-(trifluoromethyl)-2-pyridyl]-2-[(1,3-dioxo-2,3-dihydro-1H-2-isoindolyl)methyl]malonate (Compound 403)

To a suspension of 60% sodium hydride (0.65 g) in dry dimethylformamide (20 ml) at 0° C. was added a solution of diethyl 2-(3-chloro-5-trifluoromethyl-2-pyridyl)malonate (5 g) in dry dimethylformamide (10 ml) and the mixture was stirred for 15 minutes. A solution of N-bromomethylphthalimide (3.55 g) in dry dimethylformamide (10 ml) was added dropwise and the mixture was warmed with stirring to 22° C. over 18 hours. Glacial acetic acid (1 ml) was added and the mixture was poured into cold water (500 ml). The aqueous solution was extracted with diethyl ether (3×150 ml) and the combined extract was water washed (3×100 ml). The organic extract was dried (MgSO$_4$) and evaporated to give a crude product. Trituration with diethyl ether/light petroleum (b.p. 40–60° C.) (1:1) gave the title compound, m.p. 159–61° C.

Preparation of Starting Materials
Diethyl 2-(3-chloro-5-trifluoromethyl-2-pyridyl)malonate To a suspension of 60% sodium hydride in mineral oil (5.28 g) in dry dimethylformamide (50 ml) at 0° C. was added a solution of diethyl malonate (10 ml) in dry dimethylformamide (25 ml) and the mixture was stirred for 30 minutes. A solution of 2,3-dichloro-5-(trifluoromethyl)pyridine (9.8 ml) in dry dimethylformamide (10 ml) was added dropwise and the mixture warmed with stirring to 22° C. over 18 hours. Acetic acid (7.5 ml) in diethyl ether (20 ml) was added dropwise and the mixture was stirred until hydrogen evolution had ceased. The mixture was diluted with diethyl ether (600 ml) and then water washed (3×200 ml). The organic extract was dried (MgSO$_4$) and evaporated onto flash silica. Chromatography over silica eluting with 0–20% diethyl ether in light petroleum (b.p. 40–60° C.) gave the title compound. $^1$H N.M.R. (CDCl$_3$) δ(ppm) 1.28 (6H, t, 2×C$\underline{H}_3$CH$_2$), 4.30 (4H, q, 2×C$\underline{H}_2$CH$_3$), 5.24 (1H, s, C$\underline{H}$(CO$_2$Et)$_2$), 7.96 (1H, s, py-$\underline{H}$), 8.74 (1H, s, py-$\underline{H}$).

EXAMPLE 8

(Compound 501)

To a solution of O-{[3-chloro-5-(trifluoromethyl)-2-pyridyl]methyl}hydroxylamine (0.4 g) and triethylamine (0.18 g) in tetrahydrofuran (20 ml) was added 2,6-dichlorobenzoyl chloride (0.37 g). The reaction mixture was stirred for 20 hours at room temperature before filtering the solution and evaporation of the filtrate. The resulting residue was redissolved in ethyl acetate and washed successively with dilute hydrochloric acid, saturated sodium bicarbonate solution and water. The organic phase was dried, filtered and evaporated to yield the crude product which was further purified by silica gel column chromatography to give the title compound.

Preparation of Starting Material
O-{[3-Chloro-5-(trifluoromethyl)-2-pyridyl]methyl}hydroxylamine To a solution of N-hydroxyphthalimide (3.55 g) in dimethylformamide (50 ml) was added potassium carbonate (3.0 g) to give a thick yellow suspension which was stirred for 1 hour. 3-Chloro-2-chloromethyl-5-trifluoromethylpyridine (5.0 g) was added and the reaction stirred at room temperature for 20 hours. The mixture was filtered and the filtrate poured into water. The resulting white solid was isolated by filtration, washed with water, redissolved in ethyl acetate and the organic solution dried and evaporated to yield the intermediate phthalimide as a white solid. The phthalimide (2.0 g) was dissolved in methanol (20 ml) and the resulting solution treated with hydrazine hydrate (0.42 g). The reaction was left to stand for 19 hours before heating at reflux for 3 hours to yield a white precipitate. The reaction mixture was filtered and the methanol filtrate evaporated. The residue was treated with diethyl ether and refiltered. Evaporation of the filtrate yielded the title compound as a green yellow oil.

The following compounds of general formula I where Y is of formula (D) and A$^1$ is 3-Cl-5-CF$_3$-2-pyridyl, R$^1$ and R$^2$ are hydrogen and L is —O—NHC(=O)—, may be prepared by methods analogous to those of Example 8:

Compound 501 m.p. 127–9° C.

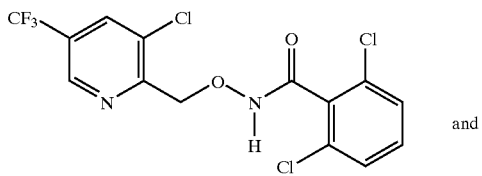

and

Compound 502 m.p. 108–10° C.

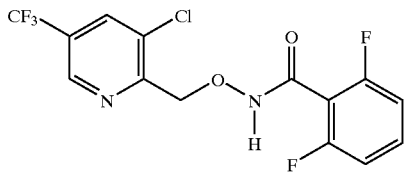

EXAMPLE 9

N-[(3-Chloro-5-trifluoromethyl-2-pyridyl)methyl]-3-(2-tolyl)propionamide (Compound 602)

To a mixture of (3-chloro-5-trifluoromethyl-2-pyridyl)methylamine hydrochloride (1 mmol, 0.247 g) in tetrahydrofuran (5 ml) was added triethylamine (2 mmol, 0.202 g) at room temperature and the mixture was stirred at room temperature for 1 hour. The mixture was filtered and the filtrate added to a solution of 3-(2-tolyl)propionyl chloride (1.1 mmol, 0.2 g) in tetrahydrofuran (5 ml) at room temperature. After 4 hours stirring at room temperature the solvent was evaporated and the residue washed with water. The solid was filtered and washed with diethyl ether/light petroleum (1:20) to give the title product, m.p. 152–3° C.

EXAMPLE 10

N-Benzyl-N'-(3-chloro-5-trifluoromethyl-2-pyridyl)methylthiourea (Compound 604)

To a mixture of (3-chloro-5-trifluoromethyl-2-pyridyl)methylamine hydrochloride (0.12 g) and benzylisothiocyanate (0.11 g) in dry tetrahydrofuran (10 ml) was added triethylamine (10 drops) and the mixture stirred at room temperature for 12 hours. The solvent was evaporated and ethyl acetate added. The mixture was washed with 2M hydrochloric acid and then with saturated sodium bicarbonate solution. The organic layer was separated and the solvent removed to give the title product. $^1$H N.M.R. δ(ppm) 4.7 (2H, broad s), 4.95 (2H, d), 6.9 (1H, broad s), 7.3–7.55 (6H, m), 7.95 (1H, s) and 8.58 (1H, s).

EXAMPLE 11

N-[(3-Chloro-5-trifluoromethyl-2-pyridyl)methyl]-2-phenylthiopropanamide (Compound 615)

A mixture of thiophenol (55 mg) and potassium tert-butoxide (56 mg) in tetrahydrofuran (5 ml) was stirred at room temperature for 30 minutes. Starting material (see below) (173 mg) was added and the mixture was heated at 65° C. with stirring for 2 hours. When cool, the mixture was evaporated and the residue was purified by silica gel chromatography to give the title product. $^1$H N.M.R. δ(ppm) 1.6 (3h, d), 3.9 (1H, q), 4.67 (2H, d), 7.25 (3H, m), 7.38 (2H, m), 7.9 (1H, s), 8.0 (1H, broad s) and 8.7 (1H, s).

Preparation of Starting Material
N-[(3-Chloro-5-trifluoromethyl-2-pyridyl)methyl]-2-bromopropionamide To a mixture of (3-chloro-5-trifluoromethyl-2-pyridyl)methylamine hydrochloride (1.0 g) in tetrahydrofuran (5 ml) and triethylamine (0.41 g) which had been stirred at room temperature for 30 minutes, was added a mixture of 2-bromopropionic acid (0.62 g) and carbonyldiimidazole (0.65 g) in tetrahydrofuran (5 ml) which had also been stirred at room temperature for 30 minutes. The combined mixture was stirred at room temperature for 12 hours and then the solvent was removed. The residue was partitioned between diethyl ether and water and the layers separated. The organic phase was dried (MgSO$_4$) and the solvent removed to give the title product.

EXAMPLE 12

3-(3-Chloro-5-trifluoromethyl-2-pyridyl)methylamino)-1-phenylbut-2-enone (Compound 610)

To a suspension of (3-chloro-5-trifluoromethyl-2-pyridyl)methylamine hydrochloride (2.5 g) in dry tetrahydrofuran (20 ml) was added anhydrous sodium acetate (1.64 g) and benzoyl acetone (1.62 g). The suspension was stirred at 20° C. for 18 hours, then heated at 50° C. for 4 hours. The mixture was evaporated and the residue partitioned between ethyl acetate and water. The organic extracts were dried (MgSO$_4$), filtered and evaporated to give a solid. The solid was triturated with diethyl ether, filtered and washed with diethyl ether to give the title product, m.p. 123–5° C.

EXAMPLE 13

3-(3-Chloro-5-trifluoromethyl-2-pyridyl)methylamino)-1-(2,6-dichlorophenyl)propenone (Compound 612)

The title compound was prepared in analogous fashion to Example 4 replacing benzoyl acetone with 1-(2,6-dichlorophenyl)-3-hydroxypropenone (see below). Purification was performed by silica gel chromatography eluting with 2% triethylamine in diethyl ether/light petroleum (b.p. 40–60° C.) (1:1) to give a mixture of E and Z isomers. $^1$H N.M.R. δ(ppm) 4.54 (2H, m, py-CH$_2$), 4.76 (2H, m, py-CH$_2$), 5.24 (1H, m, HNCH=CH), 5.60 (1H, m, HNCH=CH), 6.72 (1H, broad s, NH), 7.02–7.35 (8H, m, 2×HNCH=CH—, 6×Ar—H), 7.42 (1H, broad s, NH), 7.96 (2H, d, 2×py-H), 8.7 (1H, s, py-H), 8.86 (1H, s, py-H) and 10.5 (4H, broad s, 2×NTH$_2$Cl).

Preparation of Starting Materials
1-(2,6-Dichlorophenyl)-3-dimethylaminopropenone To a solution of 2,6-dichloroacetophenone (2 g) in dry dimethylformamide dimethyl acetal (10 ml) was added pyridinium 4-toluene sulfonate (0.2 g). The mixture was stirred under nitrogen and heated to reflux for 90 minutes. An azeotrope of dimethylformamide dimethylacetal/methanol was distilled under nitrogen to complete loss of 2,6-dichloroacetophenone by thin layer chromatography. The cold mixture was evaporated to give a solid. The solid was triturated with 10% diethyl ether in light petroleum (b.p. 40–60° C.), filtered and washed with the same to give the title compound, m.p. 98–100° C.

1-(2,6-Dichlorophenyl)-3-hydroxypropenone

To a solution of the product from stage a) (1.2 g) in acetone (20 ml) and water (2 ml) was added dry Amberlyst 15 resin (2 g) and the mixture was refluxed with stirring under nitrogen for 18 hours. The solution was vacuum filtered and the filtrate evaporated. The residue was dissolved in diethyl ether (50 ml) and dried (MgSO₄). The filtrate was presorbed onto silica gel (10 g) and purified by silica gel chromatography gradient eluting with 20 to 30% diethyl ether in light petroleum (b.p. 40–60° C.) to give the title compound.

EXAMPLE 14

(9-Fluorenylmethyl) N-[(3-Chloro-5-trifluoromethyl-2-pyridyl)methyl]carbamate (Compound 601)

A mixture of the starting material (see below) (1.97 g), dioxane (40 ml), water (20 ml) and concentrated hydrochloric acid (10 ml) was refluxed for 48 hours. On cooling, diethyl ether (100 ml) was added and the layers separated. The organic layer was washed with water (50 ml), dried (MgSO₄) and the solvent removed to give a solid which was recrystallised from toluene, m.p. 159–61° C.

Preparation of Starting Material
(9-Fluorenylmethyl) N-[(3-chloro-5-trifluoromethyl-2-pyridyl)-α-ethoxycarbonylmethyl]carbamate To a mixture of 3-chloro-5-trifluoromethyl-2-pyridyl-α-ethoxycarbonylmethyl ammonium chloride (1.91 g) in dichloromethane (25 ml) and triethylamine (0.85 ml), was added N-(9-fluorenylmethoxycarbonyloxy)succinimide (2.02 g) and the mixture was stirred at room temperature for 90 minutes. Water (15 ml) was then added and the layers separated. The aqueous phase was extracted with dichloromethane and the combined organic layers were dried (MgSO₄) and the solvent removed. The residue was purified by silica gel chromatography gradient eluting with diethyl ether/light petroleum (b.p. 40–60° C.) to give the title compound.

The following compounds of formula Ir (see Table E), i.e. compounds of general formula I where Y is of formula (E) and A¹ is 3-Cl-5-CF₃-2-pyridyl and R¹ is hydrogen, may be prepared by methods analogous to the above Examples.

TABLE E (Ir)

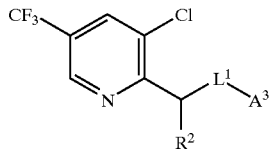

| Cmp | L¹ | R² | A³ | m.p. (° C.) |
|---|---|---|---|---|
| 601 | —NH—C(=O)O—CH₂— | H | 9-fluorenyl | 159–61 |
| 602 | —NH—C(=O)—(CH₂)₂— | H | 2-tolyl | 152–3 |
| 603 | —NH—C(=O)NH—CH₂— | H | phenyl | oil |
| 604 | —NH—C(=S)NH—CH₂— | H | phenyl | oil |
| 605 | —NH—C(=O)NH—CH₂— | H | 3-Cl-5-CF₃-2-pyridyl | 153–4 |
| 606 | —N(Et)—C(=O)CH₂O— | CO₂Et | phenyl | 96–9 |
| 607 | —NH—C(=O)CH₂O— | H | phenyl | 123 |
| 608 | —NH—C(=O)CH₂S— | H | phenyl | 102–3 |
| 609 | —NHC(=O)CH=CH— | H | phenyl | 110–1 |
| 610 | —NHC(Me)=CH—C(=O)— | H | phenyl | 123–5 |
| 611 | —NHC(=O)CH=CH— | H | 2,6-diCl-phenyl | 168–9 |
| 612 | —NHCH=CH—C(=O)— | H | 2,6-diCl-phenyl | 129 |
| 613 | —NH—C(=O)—C(Me)₂O— | H | 4-Cl-phenyl | 65 |
| 614 | —NH—C(=O)—CH(Me)O— | H | 2,6-diCl-phenyl | 131 |
| 615 | —NH—C(=O)—CH(Me)S— | H | phenyl | oil |
| 616 | —NH—C(=O)CH₂O— | H | 2,4-diCl-phenyl | 149 |
| 617 | —NH—C(=O)CH₂O— | H | 4-Cl-phenyl | 116 |
| 618 | —NH—C(=O)CH₂S— | H | 3-(4-tolyl)-1,2,4-thiadiazol-5-yl | 162 |
| 619 | —NH—C(=O)CH₂O— | H | 4-tolyl | 116 |
| 620 | —NH—C(=O)CH₂O— | H | 4-Cl-benzthiazol-2-yl | 106 |
| 621 | —NH—C(=O)CH₂O— | H | 2-biphenylyl | 93 |
| 622 | —NH—C(=O)CH₂O— | H | 3,5-diCl-2-tolyl | 100 |
| 623 | —NH—C(=O)CH₂O— | H | 2-Cl-phenyl | 82 |
| 624 | —NH—C(=O)CH₂S— | H | 4,6-diCl-3-tolyl | 118 |
| 625 | —NH—C(=O)CH₂S— | H | 4-tolyl | 109 |
| 626 | —NH—C(=O)CH(Me)O— | H | 4-Cl-phenyl | oil |
| 627 | —NH—C(=O)CH(Me)O— | H | phenyl | 88 |
| 628 | —NH—C(=O)CH(Me)O— | H | 6-Cl-3-tolyl | oil |
| 629 | —NH—C(=O)CH(Ph)O— | H | 5-Cl-2-tolyl | 150 |
| 630 | —NH—C(=O)CH(CH₂OMe)O— | H | 2,4,5-triCl-phenyl | 152 |
| 631 | —NH—C(=O)CH(Me)O— | H | 2-tolyl | 150 |
| 632 | —NH—C(=O)CH(CH₂OMe)O— | H | 2,4-diCl-phenyl | 80 |
| 633 | —NH—C(=O)CH(Et)O— | H | 4-Cl-2-OH-phenyl | 83 |
| 634 | —NH—C(=O)CH(Ph)O— | H | 2,4,5-triCl-phenyl | 138 |
| 635 | —NH—C(=O)CH(Me)S— | H | 7-CF₃-quinolin-4-yl | 131 |
| 636 | —NH—C(=O)CH(Me)S— | H | benzthiazol-2-yl | 108 |
| 637 | —NH—C(=O)CH(Me)S— | H | 3-(2-Cl-phenyl)-1,2,4-thiadiazol-5-yl | oil |
| 638 | —NH—C(=O)CH(Me)S— | H | 2-Me-1-Ph-1,2,4-triazol-3yl | oil |
| 639 | —NH—C(=O)CH(Me)S— | H | 3-Me-1,2,4-thiadiazol-5-yl | oil |
| 640 | —NH—C(=O)CH(Me)S— | H | 1-cyclohexyltetrazol-5-yl | oil |

TABLE E-continued (Ir)

| Cmp | L¹ | R² | A³ | m.p. (° C.) |
|-----|-----|-----|-----|-----|
| 641 | —NH—C(=O)CH(Me)S— | H | (2-Me-4,4-diMe-5-methylene-thiazoline) | oil |
| 642 | —NH—C(=O)CH(Me)S— | H | 5-CF₃-benzthiazol-2-yl | 120 |
| 643 | —NH—C(=O)CH(Me)S— | H | 5-Cl-benzthiazol-2-yl | 132 |
| 644 | —NH—C(=O)CH(Me)S— | H | 2-pyridyl | oil |
| 645 | —NH—C(=O)CH(Me)S— | H | 1-Me-tetrazol-5-yl | 98 |
| 646 | —NH—C(=O)CH(Me)S— | H | 4,6-diMe-pyrimidin-2-yl | 132 |
| 647 | —NH—C(=O)CH(Me)S— | H | benzoxazol-2-yl | 72 |
| 648 | —NH—C(=O)CH(Me)S— | H | 2-MeO-phenyl | 100 |
| 649 | —NH—C(=O)CH(Me)S— | H | 1-Me-imidazol-2-yl | oil |
| 650 | —NH—C(=O)CH(Me)S— | H | 1-Me-1,3,4-triazol-2-yl | 98 |
| 651 | —NH—C(=O)CH(Me)S— | H | 5-CF₃-2-pyridyl | 98 |
| 652 | —NH—C(=O)CH(Me)S— | H | 5-Me-1,3,4-thiadiazol-2-yl | oil |
| 653 | —NH—C(=O)CH(Me)S— | H | 2-(CO₂Me)-phenyl | 118 |
| 654 | —NH—C(=O)CH(Me)S— | H | 3-Cl-5-CF₃-2-pyridyl | 104 |
| 655 | —NH—C(=O)CH(Me)S— | H | 2-Cl-phenyl | 73 |
| 656 | —NH—C(=O)CH(Me)S— | H | 2,6-diCl-phenyl | 75 |
| 657 | —NH—C(=O)CH(Me)O— | H | 4-Br-3,5-diMe-phenyl | 121 |

Compound 603

¹H N.M.R. (CDCl₃) δ(ppm) 4.4 (2H, s), 4.7 (2H, s), 7.2–7.4 (5H, m), 7.9 (1H, s) and 8.65 (1H, s);

Compound 626

¹H N.M.R. (CDCl₃) δ(ppm) 1.55 (3H, d), 4.75 (3H, m), 6.8 (2H, d), 7.2 (2H, d), 7.7 (1H, br.s), 7.85 (1H, s) and 8.6 (1H, s);

Compound 628

¹H N.M.R. (CDCl₃) δ(ppm) 1.55 (3H, d), 2.3 (3H, s), 4.75 (3H, m), 6.65 (1H, m), 6.8 (1H, s), 7.2 (1H, m), 7.7 (1H, br.s), 7.85 (1H, s) and 8.6 (1H, s);

Compound 637

¹H N.M.R. (CDCl₃) δ(ppm) 1.65 (3H, d), 4.6 (2H, d), 4.65 (1H, q), 7.25–7.45 (3H, m), 7.75 (1H, s), 7.8 (1H, s), 7.9 (1H, d) and 8.3 (1H, br.s);

Compound 638

¹H N.M.R. (CDCl₃) δ(ppm) 1.55 (3H, d), 2.4 (3H, s), 4.3 (1H, q), 4.7 (2H, q), 7.3–7.5 (5H, m), 7.8 (1H, s), 8.15 (1H, s) and 8.4 (1H, br.s);

Compound 639

¹H N.M.R. (CDCl₃) δ(ppm) 1.6 (3H, d), 2.6 (3H, s), 4.6 (1H, q), 4.65 (2H, s), 7.85 (1H, s), 8.1 (1H, br.s) and 8.65 (1H);

Compound 640

¹H N.M.R. (CDCl₃) δ(ppm) 1.15–2.0 (13H, m), 4.0–4.1 (1H, m), 4.6 (2H, s), 7.8 (1H, s), 8.0 (1H, br.s) and 8.6 (1H, s);

Compound 641

¹H N.M.R. (CDCl₃) δ(ppm) 1.25 (3H, s), 1.35 (3H, s), 1.5 (3H, d), 4.45 (1H, q), 4.75 (2H, qd), 5.05 (2H, d), 7.85 (1H, s), 8.15 (1H, br.s) and 8.6 (1H, s);

Compound 644

¹H N.M.R. (CDCl₃) δ(ppm) 1.6 (3H, d), 4.5–4.75 (3H, m), 7.0 (1H, t), 7.1 (1H, m), 7.4 (1H, m), 7.8 (1H, s), 8.4 (1H, d), 8.55 (1H, s) and 8.7 (1H, br.s);

Compound 649

¹H N.M.R. (CDCl₃) δ(ppm) 1.5 (3H, d), 3.5 (3H, s), 4.15 (1H, q), 4.6 (2H, qd), 6.8 (1H, s), 7.0 (1H, s), 7.8 (1H, s), 8.65 (1H, s) and 8.75 (1H, br.s); and Compound 652

¹H N.M.R. (CDCl₃) δ(ppm) 1.6 (3H, d), 2.65 (3H, s), 4.65 (3H, m), 7.8 (1H, m), 8.15 (1H, br.s) and 8.6 (1H, s).

The following compounds of formula Is (see Table F), i.e. compounds of general formula I where Y is a formula (E) and A¹ is 3-Cl-5-CF₃-2-pyridyl, R¹ is hydrogen and L¹ is —NHC(=O)CH(R⁸)N(R⁹)—, may be prepared by methods analogous to the above Examples.

TABLE F (Is)

| Cmp | R² | R⁸ | R⁹ | A³ | m.p. (° C.) |
|-----|-----|-----|-----|-----|-----|
| 701 | H | H | H | 2-Me-benzoyl | 126 |
| 702 | H | Me (racemic) | H | benzyloxycarbonyl | 114 |
| 703 | H | Prⁱ | H | isopropyloxycarbonyl | 134 |
| 704 | H | Buⁱ | H | isopropyloxycarbonyl | 142 |
| 705 | H | Buⁱ | Me | isopropyloxycarbonyl | oil |
| 706 | Me | Prⁱ | H | isopropyloxycarbonyl | 151 |
| 707 | Me | Buⁱ | H | isopropyloxycarbonyl | 134 |
| 708 | Me | Buⁱ | Me | isopropyloxycarbonyl | oil |

TABLE F-continued

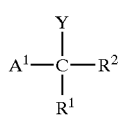
(Is)

Cmp R² R⁸ R⁹ A³ m.p. (° C.)

Compound 801 m.p. 148° C.

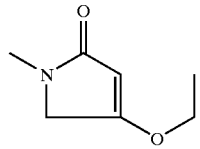

and

Compound 802 m.p. 185° C.

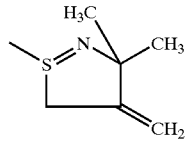

Test Example

Compounds were assessed for activity against one or more of the following:

*Phytophthora infestans*: late tomato blight
*Plasmopara viticola*: vine downy mildew
*Erysiphe graminis f* sp. *tritici*: wheat powdery mildew
*Pyricularia oryzae*: rice blast
*Leptosphaeria nodorum*: glume blotch Aqueous solutions or dispersions of the compounds at the desired concentration, including a wetting agent, were applied by spray or by drenching the stem base of the test plants, as appropriate. After a given time, plants or plant parts were inoculated with appropriate test pathogens before or after application of the compounds as appropriate, and kept under controlled environmental conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following compounds scored 2 or more against the fungi specified.

*Phytophthora infestans:* 31 and 105–7.
*Plasmopara viticola:* 50, 55, 104, 105, 201, 215, 221, 222, 224, 225, 227, 230, 232, 233, 234, 235, 328 and 606.
*Erysiphe graminis f* sp. *tritici:* 4, 25, 26, 39, 40, 44, 101, 201, 214, 304, 305, 306, 308, 310, 312, 313, 603, 606 and 642.
*Pyricularia oryzae:* 111, 112, 306, 312, 606, 624, 645, 650 and 701.
*Leptosphaeria nodorum:* 13, 105, 107, 108, 201, 229, 232, 238, 317, 336 and 626.

What is claimed is:

1. A compound or a complex or salt thereof of the general formula I:

$$A^1-\underset{\underset{R^1}{|}}{\overset{\overset{Y}{|}}{C}}-R^2 \qquad (I)$$

wherein:
$A^1$ is 2-pyridyl substituted with from one to four moieties independently selected from the group consisting of halogen and trifluoromethyl, provided that at least one moiety is trifluoromethyl;
Y is a moiety selected from the group consisting of $-L-A^2$ and $-L^1-A^3$ wherein:
$A^2$ is selected from the group consisting of unsubstituted or substituted phenyl, cyclohexyl, cyclopropyl, thienyl, imidazolyl, tolyl, and wherein any substituents on $A^2$ are independently selected from the group consisting of alkyl, halogen, and haloalkyl;
$A^3$ is selected from the group consisting of unsubstituted or substituted phenyl, pyridyl, thiodiazolyl, triazolyl, fluorenyl, tolyl, tetrazolyl, pyrimidinyl, imidazolyl, benzthiazolyl, quinolinyl, and wherein any substituents on $A^3$ are selected from the group consisting of alkyl, halogen, haloalkyl, hydroxyl, and phenyl;
L is a 3-atom linker selected from the group consisting of $-N(R^5)C(=X)N(R^6)-$, $-N(R^5)C(=X)CH(R^3)-$, $-CH(R^3)N(R^5)CH(R^4)-$, $-CH(R^3)N(R^5)C(=X)-$, $-ON(R^5)C(=X)-$; wherein the left hand side of L is attached to the central carbon atom of formula I;
$L^1$ is a 4-atom linker selected from the group consisting of $-N(R^9)C(=X)X^1CH(R^7)-$, $-N(R^9)C(=X)CH(R^7)CH(R^8)-$; $-N(R^9)C(R^7)=C(R^8)C(=X)-$, $-N(R^9)C(=X)C(R^7)(R^8)SO_2-$, and $-N(R^9)C(=X)C(R^7)(R^8)X^1$; wherein the left hand side of $L^1$ is attached to the central carbon atom of formula I;
$R^1$, $R^2$, $R^3$, and $R^4$ are independently selected from the group consisting of hydrogen or alkyl;
$R^5$, $R^6$, $R^7$, and $R^8$ are independently selected from the group consisting of hydrogen, alkyl, and acyl;
X is selected from the group consisting of oxygen and sulfur;
$X^1$ is selected from the group consisting of oxygen and $-N(R^9)-$; and $R^9$ is selected from the group consisting of hydrogen and alkyl.

2. A compound or a complex or salt thereof of the general formula I:

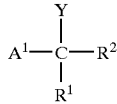   (I)

wherein:
  $A^1$ is 2-pyridyl substituted with from one to four moieties independently selected from the group consisting of halogen and haloalkyl, provided that at least one moiety is haloalkyl;
  $R^1$ and $R^2$ are independently selected from the group consisting of halogen, $R^b$, and $OR^b$;
    wherein $R^b$ is selected from the group consisting of hydrogen, alkyl, and acyl;
  Y is —L—$A^2$— wherein:
    A) L is —NHC(=X)NH—; and
      $A^2$ is selected from the group consisting of:
        1) phenyl, optionally substituted by halogen, haloalkyl, phenoxy, alkoxy, alkyl, nitro, —MeS, —$PhSO_2$, dialkylamino, alkylsulfonyl, benzylsulfonyl, S(phenyl substituted by halogen); and
        2) cyclopropyl, cyclohexyl, and naphthyl, each of which is optionally substituted by nitro; or
    B) L is —NHC(=O)CH($R^3$)—;
      wherein $R^3$ is selected from the group consisting of hydrogen, alkyl, halogen, and acyloxy; and
      $A^2$ is selected from the group consisting of:
        1) phenyl, optionally substituted by halogen, nitro, or alkoxy;
        2) thienyl;
        3) imidazolyl; and 4) 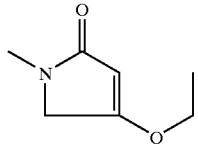

C) L is —CH($R^3$)N($R^5$)$CH_2$—
      wherein:
        $R^3$ is N-alkylcarbamoyl or alkoxycarbonyl; and
        $R^5$ is hydrogen or acyl; and
        $A^2$ is selected from the group consisting of
          1) phenyl, optionally substituted by alkyl, alkoxy, halogen, nitro, haloalkyl, or phenoxy; and
          2) naphthyl; or
    D) L is —CH($R^3$)NHC(=O)—;
      wherein $R^3$ is N-alkylcarbamoyl or alkoxycarbonyl; and
      $A^2$ is selected from the group consisting of:
        1) phenyl, optionally substituted by alkoxy, halogen, nitro, haloalkyl, phenoxy, or phenyl; and
        2) cycloalkyl; or
    E) L is —O—NHC(=O)—; and
      $A^2$ is phenyl substituted by alkyl;
  or Y is —$L^1$—$A^3$— wherein:
    A) $L^1$ is —NHC(=O)($CH_2)_2$— and $A^3$ is phenyl substituted by alkyl; or
    B) $L^1$ is —NHC(=S)$NHCH_2$—, and $A^3$ is phenyl; or
    C) $L^1$ is —NHC(=O)CH(alkyl)S— and $A^3$ is phenyl; or
    D) $L^1$ is selected from the group consisting of:
      1) —NHC(=O)$OCH_2$—,
      2) —NHC(=O)$(CH_2)_2$—,
      3) —NHC(=O)$NHCH_2$—,
      4) —NHC(=S)$NHCH_2$—,
      5) —N(alkyl)C(=O)$CH_2O$—, and
      6) —NHC(=O)$CH_2O$—;
    $R^1$ is hydrogen;
    $R^2$ is selected from the group consisting of hydrogen and alkoxycarbonyl;
    $A^3$ is selected from the group consisting of:
      1) phenyl, optionally substituted by halogen, alkyl, phenyl, or hydroxyl;
      2) fluorenyl;
      3) pyridyl, optionally substituted by halogen or haloalkyl;
      4) thiadiazolyl substituted by alkyl;
      5) benzthiazolyl, optionally substituted by halogen or by phenyl substituted by halogen;
      6) quinolinyl substituted by haloalkyl;
      7) triazolyl substituted by alkyl or phenyl;
      8) tetrazolyl substituted by alkyl or cycloalkyl;
      9) pyrimidinyl substituted by alkyl;
      10) benzoxazolyl;
      11) imidazolyl substituted by alkyl; and 12) 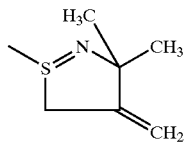

or
    E) $L^1$ is —NHC(=O)CHC$R^8$)$R^9$)—;
      $R^1$ is hydrogen;
      $R^2$, $R^8$, and $R^9$ are independently selected from the group consisting of hydrogen and alkyl; and
      $A^3$ is selected from the group consisting of
        1) benzoyl optionally substituted by alkyl, ans
        2) benzyloxycarbonyl; or
    F) $L^1$ is —NHC(=O)CH(alkyl)SO—
      $R^1$ and $R^2$ are each hydrogen; and
      $A^3$ is phenyl;
wherein the left hand sides of L and $L^1$ are attached to the central carbon atoms of formula I.

3. A fungicidal composition comprising one or more compounds as defined in claim 1, or a complex or salt thereof, in admixture with an agriculturally acceptable diluent or carrier.

4. A method of combating phytopathogenic fungi at a locus infested or liable to be infested therewith, which comprises applying to the locus a compound of the general formula I:

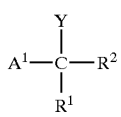   (I)

wherein:
  $A^1$ is 2-pyridyl substituted with from one to four moieties independently selected from the group consisting of halogen and haloalkyl, provided that at least one moiety is haloalkyl;

Y is a moiety selected from the group consisting of —L—A² and —L¹—A³ wherein:

A² is selected from the group consisting unsubstituted or substituted phenyl, naphthyl, cyclopropyl, cyclohexyl, biphenylyl, thienyl, imidazolyl, tolyl, and

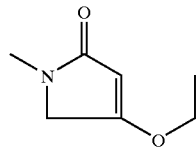

wherein:

any substituents on A² are independently selected from the group consisting of alkyl, halogen, haloalkyl, phenoxy, alkoxy, nitro, acetyl, —PhSO₂, —NMe₂, —MeSO₂, —MeS, and —PrSO₂;

A³ is selected from the group consisting unsubstituted or substituted phenyl, biphenylyl, benzoyl, benzyloxycarbonyl, isopropoxycarbonyl, benzoxazolyl, pyridyl, 2-pyridyl, thiodiazolyl, triazolyl, fluorenyl, tolyl, tetrazolyl, pyrimidinyl, imidazolyl, benzthiazolyl, quinolinyl, and

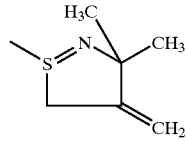

wherein:

any substituents on A³ are selected from the group consisting of alkyl, halogen, haloalkyl, hydroxyl, and phenyl;

L is a 3-atom linker selected from the group consisting of —N(R⁵)C(=X)N(R⁶)—, —N(R⁵)C(=X)CH(R³)—, —CH(R³)N(R⁵)CH(R⁴)—, —CH(R³)N(R⁵)C(=X)—, —ON(R⁵)C(=X)—; wherein the left hand side of L is attached to the central carbon atom of formula I;

L¹ is a 4-atom linker selected from the group consisting of —N(R⁹)C(=X)X¹CH(R⁷)—, —N(R⁹)C(=X)CH(R⁷)CH(R⁸)—; —N(R⁹)C(R⁷)=C(R⁸)C(=X)—, —N(R⁹)C(=X)C(R⁷)(R⁸)SO₂—, and —N(R⁹)C(=X)C(R⁷)(R⁸)X¹; wherein the left hand side of L¹ is attached to the central carbon atom of formula I;

R¹, R², R³, R⁴, R⁷, and R⁸ are independently selected from the group consisting of halogen, R$^b$, and OR$^b$;

R⁵ and R⁶, which may be the same or different, are R$^b$;

R$^b$ is selected from the group consisting of hydrogen, alkyl, and acyl;

X is selected from the group consisting of oxygen and sulfur;

X¹ is selected from the group consisting of oxygen and —N(R⁹)—;

R⁹ is R$^b$;

or a complex or salt thereof.

5. The method of claim 4 wherein the compound is applied at an application rate of from 5 to 1000 grams per hectare.

* * * * *